United States Patent
de Carvalho e Silva Santos et al.

(10) Patent No.: US 9,499,788 B2
(45) Date of Patent: Nov. 22, 2016

(54) CELL LINE OF LYMPHOCYTES COMPRISING GAMMA-DELTA T CELLS, COMPOSITION AND PRODUCTION METHOD THEREOF

(75) Inventors: Bruno Miguel de Carvalho e Silva Santos, Lisboa (PT); Daniel Vargas Correia, Corroios (PT)

(73) Assignee: INSTITUTO DE MEDICINA MOLECULAR, Lisbon (PT)

( * ) Notice: Subject to any disclaimer, the term of this patent is extended or adjusted under 35 U.S.C. 154(b) by 2 days.

(21) Appl. No.: 14/118,863

(22) PCT Filed: May 21, 2012

(86) PCT No.: PCT/IB2012/052545
§ 371 (c)(1),
(2), (4) Date: Feb. 5, 2014

(87) PCT Pub. No.: WO2012/156958
PCT Pub. Date: Nov. 22, 2012

(65) Prior Publication Data
US 2014/0141513 A1 May 22, 2014

(30) Foreign Application Priority Data
May 19, 2011 (PT) .......................................... 105714

(51) Int. Cl.
*C12N 5/0783* (2010.01)

(52) U.S. Cl.
CPC ....... *C12N 5/0636* (2013.01); *C12N 2501/998* (2013.01)

(58) Field of Classification Search
CPC .......................... C12N 5/063; C12N 2501/998
See application file for complete search history.

(56) References Cited

PUBLICATIONS

Siegers et al., Cytotherapy, 2011; 13: 753-764, doi: 10.3109/14653249.2011.553595. Epub Feb. 11, 2011.*
Correia et al. (2011), Differentiation of human peripheral blood Vδ1+ T cells expressing the natural cytotoxicity receptor NKp30 for recognition of lymphoid leukemia cells. *Blood*, 118(4), 992-1001.
Lilienfeld-Toal et al. (2006). Activated γδ T cells express the natural cytotoxicity receptor natural killer p44 and show cytotoxic activity against myeloma cells. *Clinical and Experimental Immunology*, 144(3), 528-533.
Toka et al. (2011). Rapid and Transient Activation of γγδ T Cells to IFN-γ Production, NK Cell-Like Killing, and Antigen Processing during Acute Virus Infection. *The Journal of Immunology*, 186(8), 4853-4861.
Johnson et al. (2008). Bovine WC1 γγδT cells incubated with IL-15 express the natural cytotoxicity receptor CD335 (NKp46) and produce IFN-γ in response to exogenous IL-12 and IL-18. *Developmental and Comparative Immunology*, 32(8), 1002-1010.
Stewart et al. (2007) Germ-line and rearranged *Tcrd* transcription distinguish *bona fide* NK cells and NK-like γγδ T cells. *European Journal Immunology*, 37(8), 1442-1452.
Vitale et al. (1998). NKp44, a Novel Triggering Surface Molecule Specifically Expressed by Activated Natural Killer Cells, Is Involved in Non-Major Histocompatibility Complex-restricted Tumor Cell Lysis. *The Journal of Experimental Medicine*, 187(12), 2065-2072.
Pende et al. (1999). Identification and Molecular Characterization of NKp30, a Novel Triggering Receptor Involved in Natural Cytotoxicity Mediated by Human Natural Killer Cells. *The Journal of Experimental Medicine*, 190(10), 1505-1516.
Pessino et al. (1998). Molecular Cloning of NKp46: A Novel Member of the Immunoglobulin Superfamily Involved in Triggering of Natural Cytotoxicity. *The Journal of Experimental Medicine*, 188(5), 953-960.
International Search Report, mailed Dec. 5, 2012 in connection with PCT International Application No. PCT/IB2012/052545, filed May 21, 2012.
Written Opinion of the International Searching Authority, mailed Dec. 5, 2012 in connection with PCT International Application No. PCT/IB2012/052545, filed May 21, 2012.

* cited by examiner

*Primary Examiner* — Daniel C Gamett
(74) *Attorney, Agent, or Firm* — John P. White; Cooper & Dunham LLP

(57) ABSTRACT

The present invention relates to a cell line of lymphocytes comprising γδ T cells, composition and production method thereof, and medical use namely for the use in medicine, namely in cancer immunotherapy.
The cell line comprise a sample of human peripheral blood Vδ1+ γδ T cells expressing functional natural cytotoxicity receptors (NCRs). These Vδ1+ NCR+ T lymphocytes can directly mediate killing of leukemia cell lines and chronic lymphocytic leukemia patient neoplastic cells.
The present invention shows that human Vδ1+ NCR+ T cells can be differentiated and expanded from total γδ peripheral blood lymphocytes (PBLs), upon regular in vitro or ex vivo stimulation with γδTCR agonists and γc-family cytokines. This subset surprisingly expresses NKp30, NKp44 and NKp46, and high levels of Granzyme B that associate with highly enhanced cytotoxicity against lymphoid leukemias.

23 Claims, 18 Drawing Sheets

CELL LINE OF LYMPHOCYTES COMPRISING GAMMA-DELTA T CELLS, COMPOSITION AND PRODUCTION METHOD THEREOF

CROSS-REFERENCE TO RELATED APPLICATIONS

This application is a §371 national stage of PCT International Application No. PCT/IB2012/052545, filed May 21, 2012, claiming priority of Portuguese Patent Application No. 105714, filed May 19, 2011, the contents of each of which are hereby incorporated by reference in their entirety.

REFERENCE TO SEQUENCE LISTING

This application incorporates-by-reference nucleotide and/or amino acid sequences which are present in the file named "131119_5126_85759_Substitute_Sequence_Listing_BI.txt," which is 2.40 kilobytes in size, and which was created Nov. 19, 2013 in the IBM-PC machine format, having an operating system compatibility with MS-Windows, which is contained in the text file filed Nov. 19, 2013 as part of this application.

TECHNICAL FIELD OF THE INVENTION

The invention relates to a cell line of lymphocytes comprising γδ T cells, composition and production method thereof, and medical use namely for the use in medicine, namely in cancer immunotherapy.

BACKGROUND

Tumors develop in hosts endowed with a highly complex immune system that includes various lymphocyte subsets capable of recognizing and destroying transformed cells. It is now widely accepted that, while lymphocytes may constantly patrol tumor formation, cancer cells develop molecular strategies to evade immune surveillance, which are competitively selected under the pressure of the host immune system. This dynamic process, termed "cancer immunoediting", is thought to constitute a major obstacle to cancer immunotherapy.

Among multiple immune evasion mechanisms, it was recently shown that leukemia and lymphoma primary samples often down-regulate the non-classical MHC (major histocompatibility complex) protein, ULBP1, which is critical for recognition of hematological tumors by γδ T-cells expressing the counter-receptor NKG2D (Lanca, T. et al., "The MHC class Ib protein ULBP1 is a nonredundant determinant of leukemia/lymphoma susceptibility to gammadelta T-cell cytotoxicity", Blood 115:2407-2411; 2010).

γδ T-cells are innate-like lymphocytes that account for 1-10% of peripheral blood lymphocytes (PBL) of healthy individuals and are capable of targeting a significant fraction of hematological tumor cell lines tested in the laboratory. However, it was demonstrated that many lymphoid leukemia primary samples are resistant to fully-activated Vγ9Vδ2 T-cells (Lanca, T. et al., "The MHC class Ib protein ULBP1 is a nonredundant determinant of leukemia/lymphoma susceptibility to gammadelta T-cell cytotoxicity", Blood 115: 2407-2411, 2010; Gomes, A. Q. et al., "Identification of a panel of ten cell surface protein antigens associated with immunotargeting of leukemias and lymphomas by peripheral blood gammadelta T cells", Haematologica 95:1397-1404, 2010), the dominant subset of γδ PBLs. Furthermore, clinical trials involving the in vivo administration of activators of Vγ9Vδ2 T-cells have shown limited success, with objective responses restricted to 10-33% of patients with either hematological or solid tumors. Even more modest has been the outcome of trials involving the adoptive transfer of activated/expanded Vδ2+ cells, since no objective responses have been reported. In fact, the simple ex vivo expansion of autologous Vδ2+ T-cells, whose surveillance the tumor managed to escape in vivo, may be condemned to little therapeutic effect upon re-injection into the patient.

Cancer immunotherapy relies on tumor cell recognition by cytotoxic lymphocytes. γδ T-cells are a population of MHC-unrestricted killer lymphocytes that play critical roles in various animal tumor models. This notwithstanding, it was showed that a large proportion of human hematological tumors is resistant to γδ peripheral blood lymphocytes (PBLs) activated with specific agonists to the highly prevalent Vγ9Vδ2 T-cell receptor (TCR). This likely constitutes an important limitation to current γδ-T-cell-mediated immunotherapy.

Therefore, it is critical to invest in strategies that endow γδ T-cells with additional recognition machinery to detect tumors that have resisted the natural components present in vivo.

Natural cytotoxicity receptors were identified by A. Moretta and co-workers over a decade ago, and were shown to play critical synergistic roles in the anti-tumor functions of Natural Killer (NK) cells. In fact, NKp30 and NKp46 are widely considered to be two of the most specific NK cell markers.

The document written by von Lilienfeld-Toal, M., J. Nattermann, et al. (2006). "Activated gammadelta T cells express the natural cytotoxicity receptor natural killer p 44 and show cytotoxic activity against myeloma cells." Clin Exp Immunol 144(3): 528-533. discloses the expression of a NK receptor on peripheral blood γδ T lymphocytes. However, disclosed γδ T cells are different from those stated in the present invention. The document also reveals, contrary to the present invention, that NKp30 is not expressed in such γδ T cells. Some of differences are:

The treatment (IFN-γ, TNF-α+anti-CD3 monoclonal antibody+IL-1β+IL-2+IL-15);

The phenotype of γδ T cells (NKp30 and NKp46 moreover, 62% of γδ T cells belong to the Vδ2+ subtype;

Less than 20% of the γδ T cells are CD56+;

Less than 20% of the γδ T cells are CD8+;

The expression levels of NKp44 are not modulated by stimulation of the γδTCR/CD3 complex (thus, different molecular mechanisms are involved that induce NKp44 expression on those cells)

This document describes peripheral blood γδ T cells expressing NKp44. NKp44 was functional and was involved in the recognition and elimination of tumor cells (myeloma cells). However, only 8±7% of γδ T cells expressed NKp44 and most (62%) of γδ T cells belonged to the Vδ2+ subtype (they were Vδ1−). NKp30 and NKp46 were not expressed by γδ T cells, and less than 20% of these cells were CD8+ or CD56+.

Thus, the γδ T cell line described is totally different from our identified γδ T cell line: typically more than 95% of γδ T cells in our cell line belong to the Vδ1+ subtype and a high percentage of these Vδ1+ γδ T cells (typically more than 30%) express functional NKp44. Importantly, NKp44 demonstrate synergism with NKp30 to greatly enhance the ability to recognize and kill tumor cells (FIG. 5B). This cooperation between NCR is critical to obtain the desired effect (elimination of cancer disease), and is absent in the previously identified NKp44+ γδ T cells.

The document written by Rey, J., C. Veuillen, et al. (2009). "Natural killer and gammadelta T cells in haematological malignancies: enhancing the immune effectors." *Trends Mol Med* 15(6): 275-284. discloses the common expression of the NKG2D receptor on NK cells and on γδ T cells. This document also states that the expansion and activation of γδ T cells can generate anti-tumor responses. However, contrary to the present invention the γδ cells are NKp30⁻ and NKp46⁻.

The document WO 00/44893 (Palmetto Richland Memorial Hos) discloses a method of treatment of leukemia based on the administration of substantially purified γδ T lymphocytes. The method comprises the preparation of lymphocyte activation and expansion thereof. The main differences are:

The treatment (plate-bound immobilized anti-TCR antibodies+irradiated "feeder" tumor B-cells);
/The γδ T cells (NKp30⁻, NKp44⁻, NKp46⁻, CD8⁻).

The document WO 2011/053750 (Emory University) discloses a method of reducing cancer in a patient, comprising the steps of isolating a population of cytotoxic cells, like γδ T cells; administration of the therapeutic agent and the cytotoxic cells. The main difference to present invention is that γδ T cells are genetically modified to resist chemotherapeutic agents.

SUMMARY

The present invention relates to a cell line of peripheral blood lymphocytes comprising or consisting of Vδ1+ γδ T cells expressing functional natural cytotoxicity receptors (NCR). In a more preferred embodiment, the natural cytotoxicity receptors comprise or consist of NKp30.

In a more preferred embodiment, the cell line disclosed could further comprise Vδ2+ γδ T cells.

Another more preferred embodiment of the cell line disclosed, the natural cytotoxicity receptors could further comprise NKp44, NKp46, or mixtures thereof.

Another preferred embodiment of the cell line disclosed, the cell line could express granzime B.

The disclosed subject matter further includes a composition with the said cell line. In a preferred embodiment, the composition is an injectable. In a preferred embodiment the injectable composition comprises a cell population composed of more than 80%, namely more than 80%, 85%, 90%, 95%, of functional Vδ1+ γδ T cells expressing functional natural cytotoxicity receptors, more preferably the natural cytotoxicity receptors comprise or consist of NKp30 and, wherein it comprises more than 100 million of Vδ1+ γδ T cells expressing functional natural cytotoxicity receptors. Preferably the composition also comprises a pharmaceutically acceptable agent or carrier and, more preferably, a stabilizing agent, namely as human serum albumin. The cells are preferably autologous, that is to say, derived from a same biological preparation (or from a same donor). More preferably, they are obtained by a method such as method described by disclosed subject matter.

Another aspect of the disclosed subject matter is the use in medicine of composition that comprises cells of the cell line disclosed in the present invention.

In a more preferred embodiment, the composition disclosed in the present invention could be used in autologous or heterologous adoptive cell therapy, tumor or cancer treatment, tumor or cancer immunotherapy, and/or leukemia treatment, or for treatment of acute lymphoblastic leukemia, acute myelogenous leukemia, chronic myelogenous leukemia, chronic lymphocytic leukemia, multiple myeloma, burkitt's lymphoma, follicular lymphoma, breast carcinoma, lung carcinoma, prostate carcinoma, colon carcinoma, bladder carcinoma, renal cell carcinoma, or skin melanoma, among others.

In a more preferred embodiment, the composition disclosed in the present invention could be used in the treatment of a viral infection. Namely, when the virus treated is from the family Herpesviridae or Retroviridae, among others.

The disclosed subject matter further includes a method of producing the cell line described which comprises isolating γδ PBLs. In a preferred embodiment, the starting sample could be blood including peripheral blood sample or fractions thereof, including buffy coat cells, mononuclear cells and low density mononuclear cells. The cells may be obtained from a starting sample of blood using techniques known in the art such as density gradient centrifugation. Total γδ PBLs can be isolated via positive selection with magnetic-labeled anti-TCRγδ+ antibodies or through depletion/elimination of TCRγδ⁽⁻⁾ cells. γδ PBL can be maintained in any suitable mammalian cell culture medium such as RPMI 1640 or IMDM.

The disclosed subject matter further includes a method of cultivating these cells in an adequate culture medium in the presence of γδTCR agonists, preferably by regular addition (more preferably continuous addition) of said agonists, preferably soluble or immobilized, and in the presence of at least one γc-cytokine, preferably by regular addition (more preferably continuous addition) of said cytokine or cytokines. The said γδTCR agonists and γc-cytokines are added to said culture of cells at the time of the culturing and also throughout the culturing period, preferably every 3-6 days, so that the concentration of γδTCR agonists and γc-cytokines in the said culture is always typically more than zero.

In a preferred embodiment, the addition of said γδTCR agonists and γc-cytokines could be carried out until at least 40% of the cells express natural cytotoxicity receptors, more preferably at least 50%, 60%, 70%, 75%, 80%, 85%, 95%. In a more preferred embodiment, the addition of said γδTCR agonists and γc-cytokines could be carried out until it is achieved more than 50 million, more than 100 million, more than 200 million of viable and functional cells that express natural cytotoxicity receptors, namely the natural cytotoxicity receptors comprise or consist of NKp30.

In a more preferred embodiment of the disclosed method, the addition of said γδTCR agonists and γc-cytokines could be carried out until at least 40% of the cells express NKp30, more preferably at least 50%, 60%, 70%, 75%, 80%, 85%, 95%, 100%.

In other preferred embodiment of the disclosed method, the γδTCR agonist can be any soluble or immobilized molecule or compound that is able to activate, stimulate or trigger the γδTCR/CD3 receptor complex expressed in all Vδ1+ γδ PBL, including, but not limited to, plant lectins (including phytohemagglutinin-PHA), anti-CD3 monoclonal antibodies (including OKT3 mAb), anti-γδTCR monoclonal antibodies or mixtures thereof. Other agonist antibodies to the Vδ1+ γδTCR can be used. The term "antibodies" include monoclonal antibodies, polyclonal antibodies, antibody fragments, single chain antibodies, single chain variable fragments and recombinantly produced binding partners. More preferably, the range of γδTCR agonist concentration could vary between 0.01-100 μg/ml, even more preferably between 1-5 μg/ml.

In a more preferred embodiment of the disclosed method the said "γc-cytokine" means common cytokine receptor gamma-chain family of cytokines, preferably interleukin, namely IL-2, IL-4, IL-7, IL-9, IL-12, IL-15, IL-21 or mixtures thereof, among others. The interleukin used may be of human or animal origin, preferably of human origin. It may be a wild-type protein or any biologically active fragment or variant, that is, to say, capable of binding its receptor and inducing activation of γδ T cells in the conditions of the method according to the invention. More preferably, the cytokines may be in soluble form, fusioned or complexed with another molecule, such as for example a peptide, polypeptide or biologically active protein. Preferably, a human recombinant γc cytokine is used. More preferably, the range of interleukin concentration could vary between 1-10000 U/ml, even more preferably between 100-1000 U/ml.

In other preferred embodiment of the disclosed method the regular addition of said γδTCR agonists and γc-cytokines could be performed for 2-60 days, more preferably between 9-25 days, even more preferably between 10-15 days, namely 11, 12, 13, 14 days.

GENERAL DESCRIPTION OF THE INVENTION

The present invention describes a cell line of peripheral blood lymphocytes comprising γδ T cells, composition and production method thereof, preferentially expressing NKp30, NKp44 and NKp46, for use in medicine, namely in cancer immunotherapy.

The present invention discloses a novel subset of Vδ2$^{(-)}$ Vδ1$^+$ γδ PBLs expressing natural cytotoxicity receptors (NCRs) that directly mediate killing of leukemia cell lines and chronic lymphocytic leukemia patient neoplastic cells. Is shown that NCR$^+$ Vδ1$^+$ T-cells can be differentiated and expanded from total γδ PBL upon stimulation with γc-cytokines and pan-TCR agonists, through a process that requires functional PI-3K/AKT signaling. Surprisingly, this subset stably expresses NKp30, NKp44 and NKp46, and high levels of Granzyme B that associates with enhanced cytotoxicity against lymphoid leukemia cells. Specific gain-of-function and loss-of-function experiments demonstrate that NKp30 and NKp44, but not NKp46, play non-redundant and synergistic roles in TCR-independent leukemia cell recognition. Thus, NCR$^+$ Vδ1$^+$ T-cells constitute an inducible and specialized killer lymphocyte population for adoptive cell immunotherapy of human cancer.

DESCRIPTION OF THE FIGURES

The following figures provide preferred embodiments for illustrating the description and should not be seen as limiting the scope of invention.

Figure 1A:
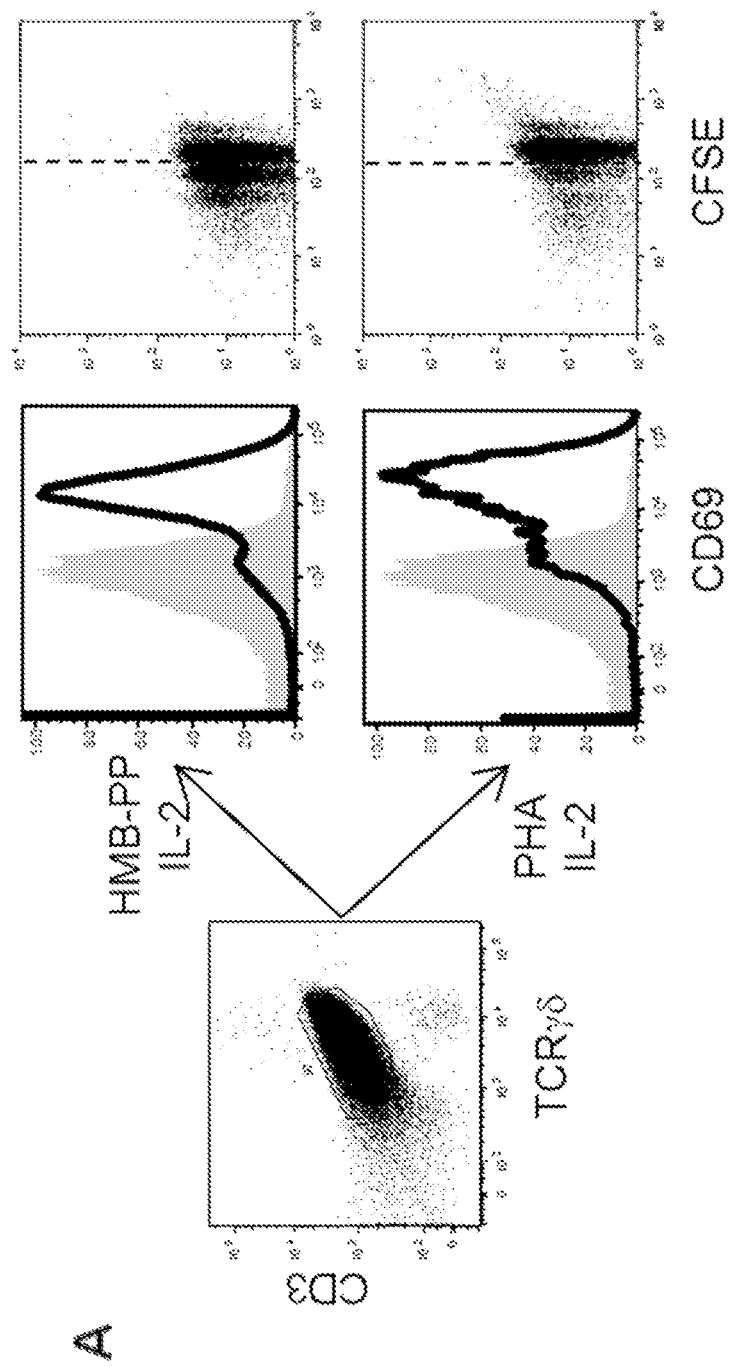
FIG. 1a, 1b, 1c—Enhanced anti-leukemia cytotoxicity of γδ PBL cultures activated with pan-T-cell mitogen. (A) γδ peripheral blood lymphocytes (γδ PBLs) were MACS-sorted from the peripheral blood of healthy volunteers (left panel), and stimulated with either HMB-PP/IL-2 or PHA/IL-2 for 4-19 days. Activation was evaluated by flow cytometry for CD69 upregulation (middle panels; levels in freshly-isolated control cells are shaded) and CFSE dilution (right panels; dotted line indicates initial CFSE levels). (B-C) Pre-activated (for 14 days, as in A) γδ PBL were co-incubated with DDAOse-labeled leukemia cells for 3 hours. Tumor cell lysis was evaluated by Annexin-V staining using flow cytometry. (B) Representative results of 6 different donors for the Bv173 leukemia cell line. Percentages refer to Annexin-V$^+$ tumor cells. Basal tumor cell apoptosis (in the absence of γδ PBL) was <5%. (C) Summary of the results of 6 different donors with 4 leukemia target cell lines. Error bars represent SD (n=6, *p<0.05; **p<0.01). (D) Real-time PCR quantification of GzmB mRNA levels in freshly-isolated, HMB-PP/IL-2-activated and PHA/IL-2-activated γδ PBL. Data in this figure are representative of 2-3 independent experiments with similar results.
Figure 6A:
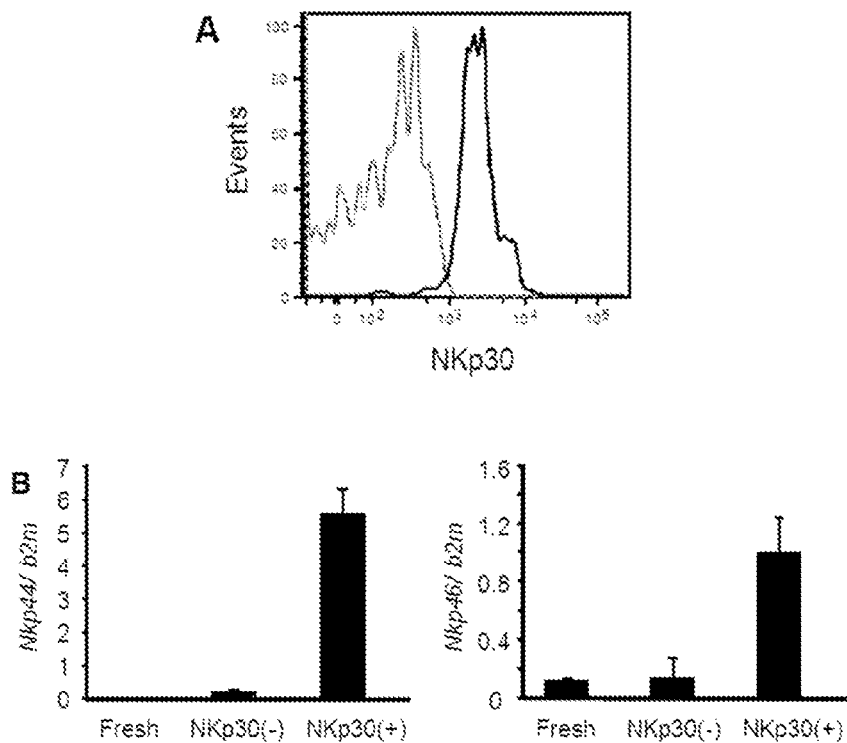
Figure 6B:
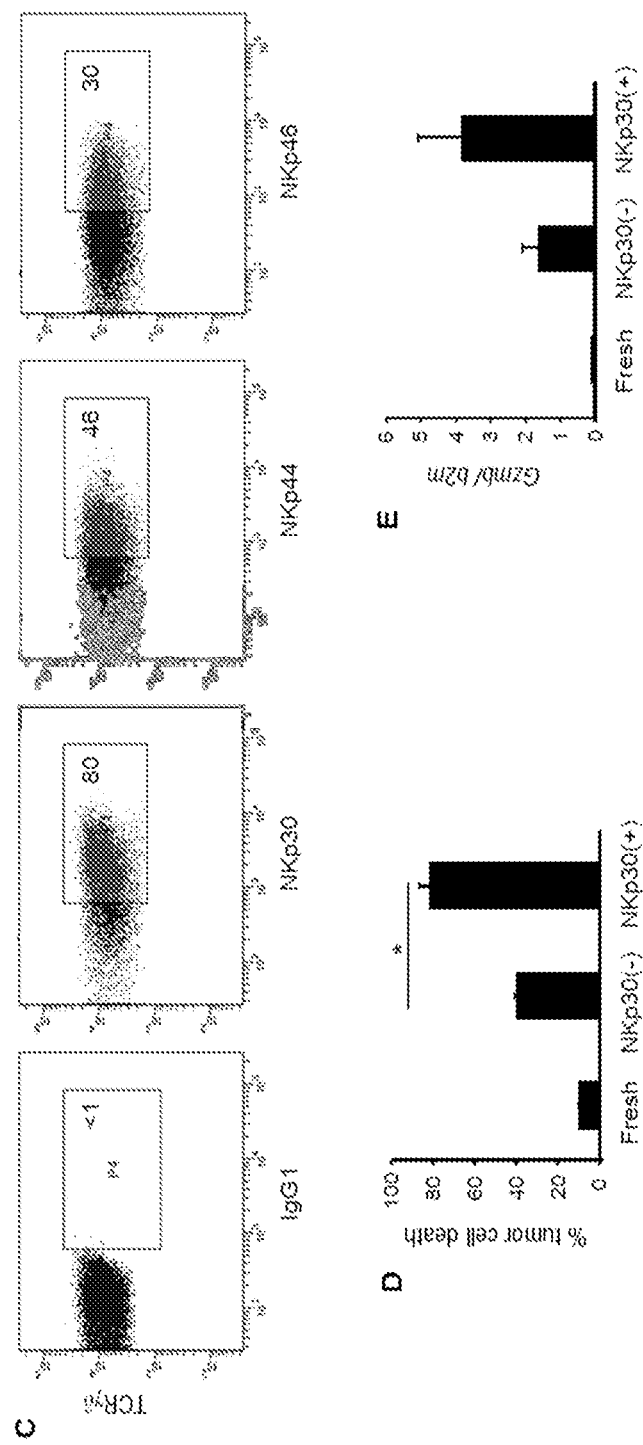
Figure 6C:
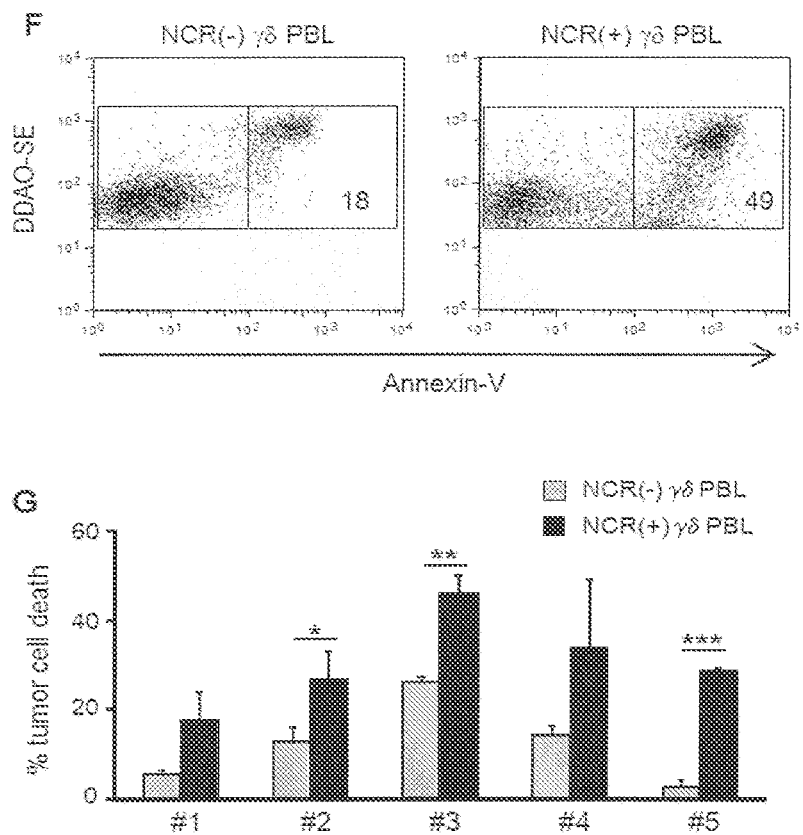

FIGS. 6a, 6b, 6c—NCR+ γδ PBLs are a stable subset endowed with enhanced cytotoxicity against primary lymphocytic leukemias. NKp30$^+$ and NKp30$^{(-)}$ γδ PBLs were FACS-sorted from 14-day PHA/IL-2-activated cultures. (A) Re-analysis of NKp30 expression in the purified populations. (B) Real-time PCR quantification of Nkp44 (left) and Nkp46 (right) mRNA levels in NKp30$^{(-)}$ or NKp30$^+$ γδ T-cells, compared to freshly-isolated γδ PBLs. Error bars represent SD (n=3). (C) Sorted NKp30$^+$ γδ PBLs were cultured in the presence of IL-2. Analysis of NKp30$^{(-)}$ NKp44 and NKp46 expression after days. (D) NKp30$^{(-)}$ or NKp30$^+$ γδ T-cells, or freshly-isolated γδ PBLs, were used in killing assays with the leukemia cell line Bv173 (as in FIG. 1). Tumor cell death was evaluated by Annexin-V staining (n=3, *p<0.05). (E) Real-time PCR quantification of GzmB mRNA levels in freshly-isolated, NKp30$^{(-)}$ or NKp30$^+$ γδ T-cells. Error bars represent SD (n=3). (F-G) Representative plots (F) and data summary (G) for 5 primary B-cell chronic lymphocytic leukemia samples that were used in killing assays (as in FIG. 1) with γδ PBLs obtained from 6 distinct donors and activated with either HMB-PP/IL-2 or PHA/IL-2. NCR$^{(-)}$γδ PBL from HMB-PP/IL-2-activated cultures (grey bars) were compared to NCR$^{(+)}$ γδ PBL from PHA/IL-2-activated cultures (black bars). Error bars represent SD (n=6, *p<0.05; p<0.01; *p<0.001).

Figure 7:
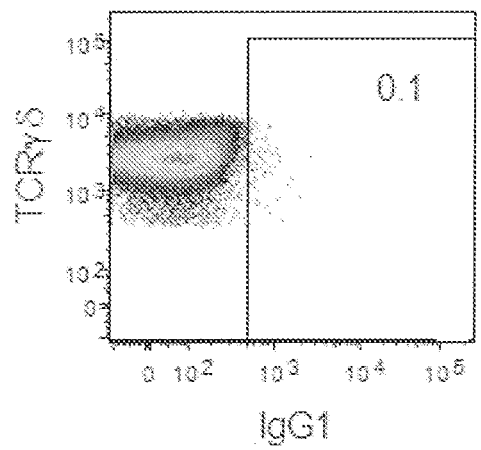

FIG. 7—Isotype control staining for NKp30 in PHA/IL-2-activated γδ PBLs. Flow cytometry IgG1 staining in gated TCRγδ$^+$ cells from PBL cultures described in FIGS. 1-2. Data are representative of 6 independent experiments.

Figure 8:
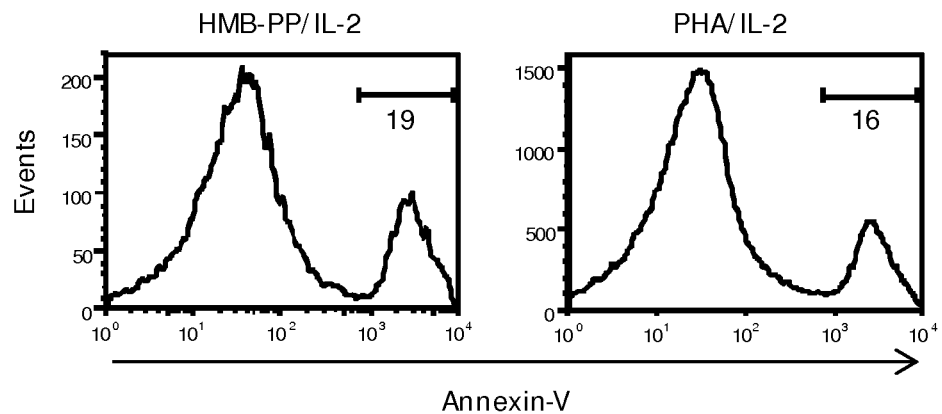

FIG. 8—Vγ9Vδ2 PBLs are not preferentially susceptible to PHA-induced apoptosis. γδ PBLs were cultured with HMB-PP/IL-2 or PHA/IL-2 as described in FIGS. 1 and 3. Apoptotic Annexin-V$^+$ cells within pre-gated Vδ2$^+$ cells were analyzed after 7 days in culture by flow cytometry.

Figure 9:
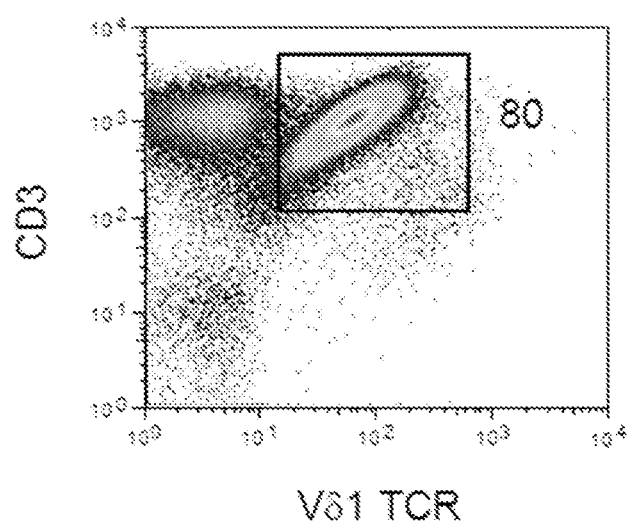

FIG. 9—Vδ1$^+$ T-cell enrichment in γδ PBL cultures activated with PHA/IL-2. γδ PBLs were cultured with PHA/IL-2 for 19 days, as described in FIGS. 1 and 3, and analyzed by flow cytometry for Vδ1 TCR and CD3 expression.

Figure 10:
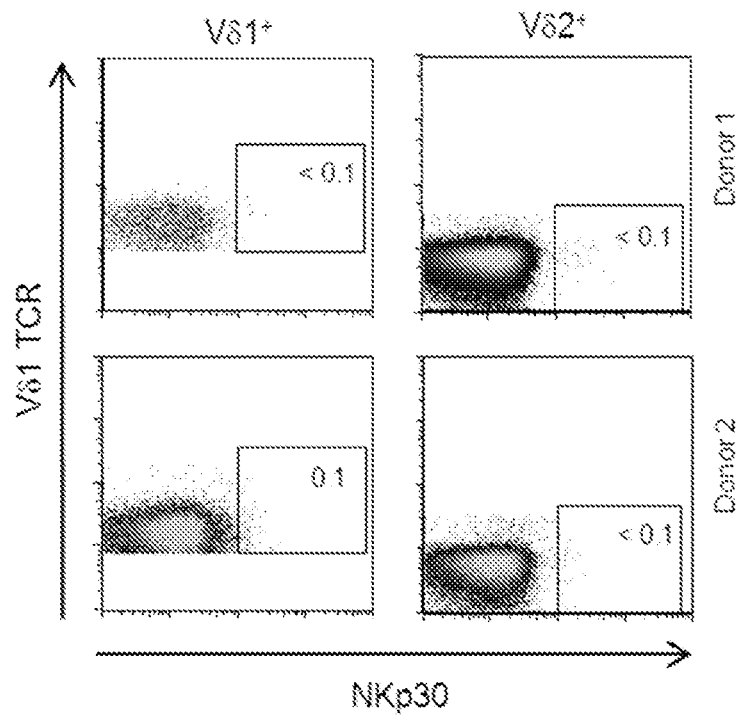

FIG. 10—Freshly-isolated γδ PBLs do not express NKp30. Flow cytometry data for NKp30 and Vδ1 TCR expression in γδ PBLs freshly-isolated from two healthy donors. Data are representative of fifteen different healthy donors.

Figure 11:
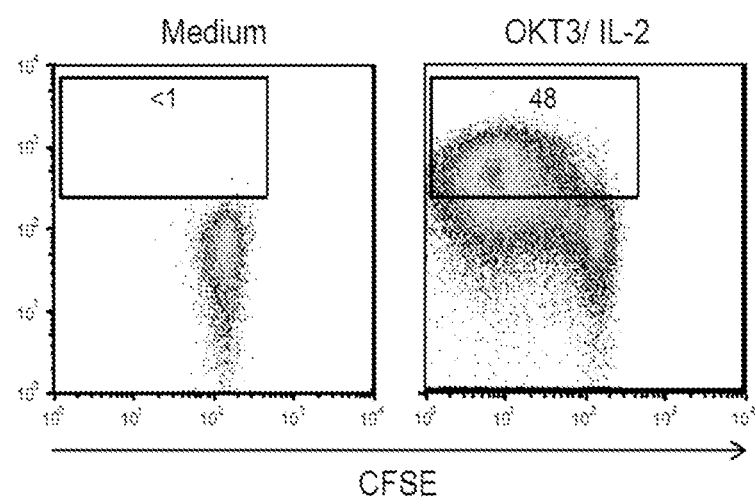

FIG. 11—TCR plus IL-2 signals induce NKp30 expression in proliferating Vδ1$^+$ T-cells. NKp30 expression in Vδ1$^+$ T-cells, FACS-sorted from peripheral blood, labeled with CFSE and cultured with or without OKT3 mAb and IL-2 for 7 days.

Figure 12:
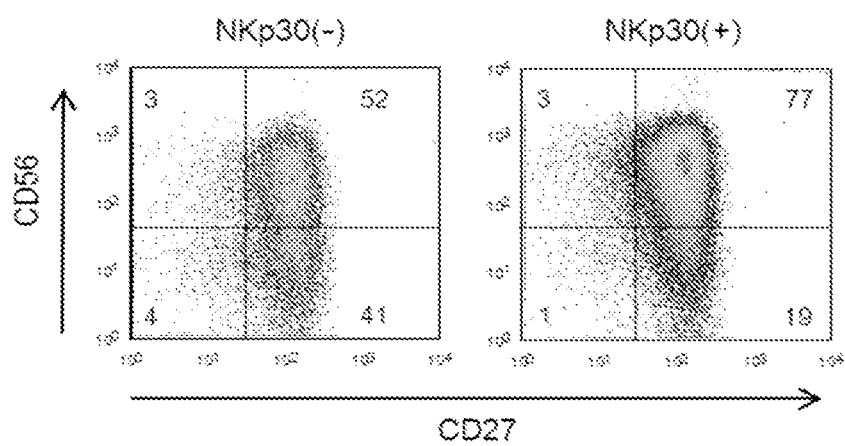

FIG. 12—Increased expression of CD56 in NCR$^+$ Vδ1$^+$ PBLs. Flow cytometry data for CD56 and CD27 expression in Vδ1$^+$ PBLs activated with PHA/IL-2 for 19 days and gated on either NKp30$^{(-)}$ or NKp30$^+$ cells.

Figure 13:
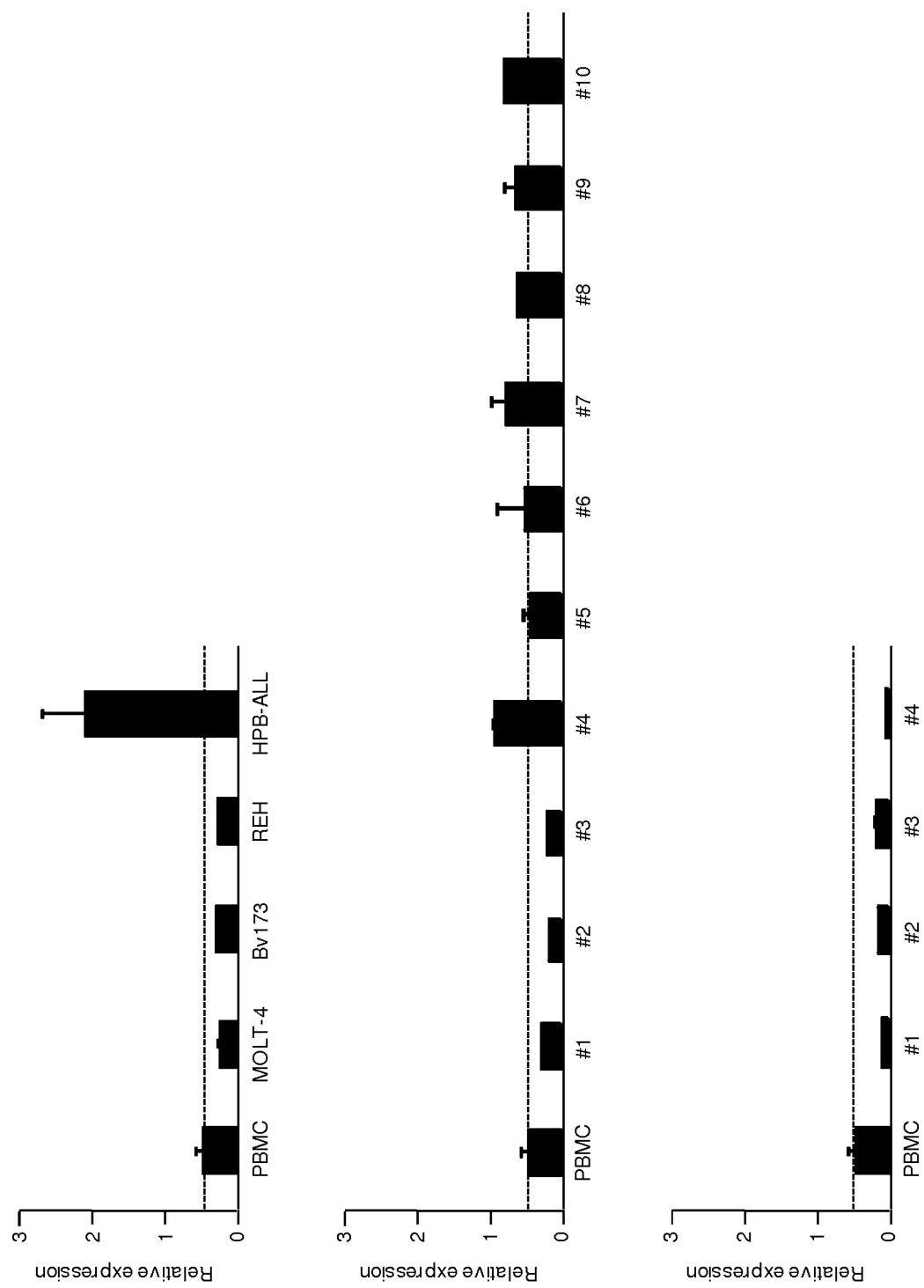

FIG. 13—B7h6 is not overexpressed in most lymphoid leukemia samples. Real-time quantitative PCR data for B7h6 expression on (A) acute lymphoblastic leukemia cell lines; (B) T-cell acute lymphoblastic leukemia patient samples; (C) B-cell chronic lymphocytic leukemia patient samples. Healthy fresh PBMC are shown as reference (dashed line). B7h6 levels were normalized to the housekeeping genes Gusb and Psmb6 and are expressed in arbitrary units. Error bars represent SD of triplicate measurements.

Figure 14:
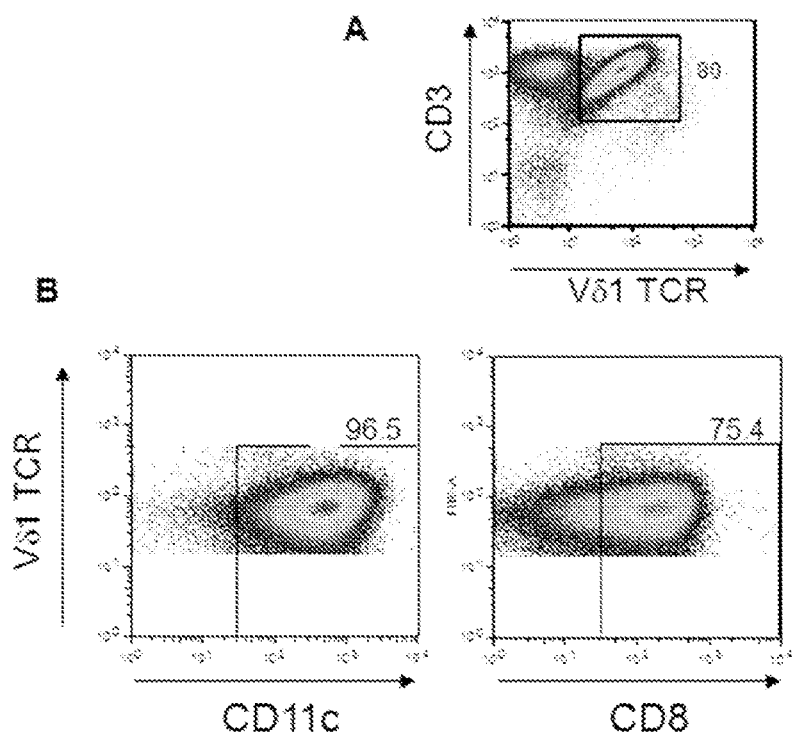

FIG. 14—Phenotype of γδ PBLs in PHA/IL-2-activated cultures. γδ PBLs were cultured with PHA/IL-2 for 19 days, as described in FIGS. 1 and 3, and analyzed by flow cytometry for (A) Vδ1 TCR and CD3 expression; (B) CD11c and CD8 expression. PHA/IL-2-activated cells are depicted in full line.

Figure 15:
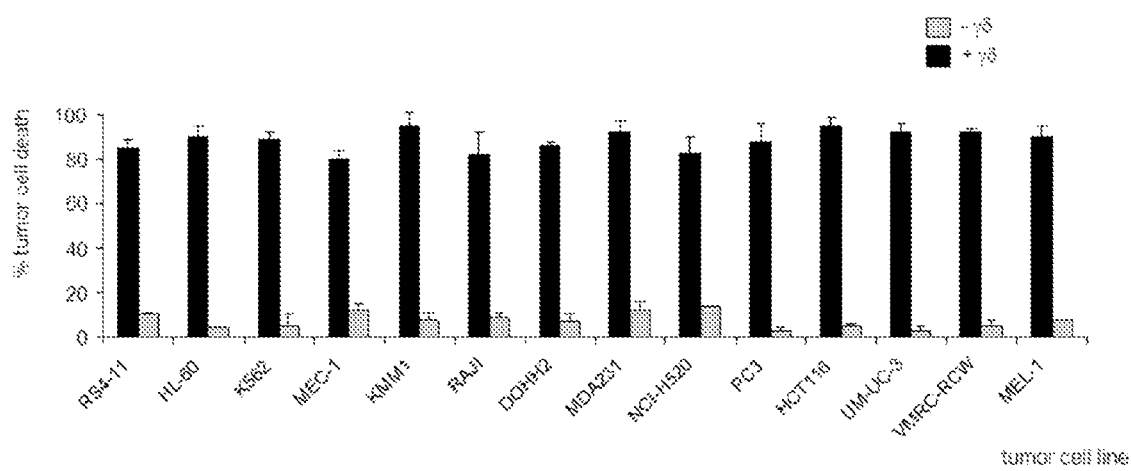

FIG. 15—NKp30$^+$ γδ PBLs are highly cytotoxic against cancer cells from diverse tissue origins. γδ peripheral blood lymphocytes (γδ PBLs) were MACS-sorted from the peripheral blood of healthy volunteers, and stimulated with PHA/IL-2 for 2 weeks. NKp30$^+$ γδ PBLs were further FACS-sorted and used in a 3 h killing assays with a panel of tumor cell lines: Acute lymphoblastic leukemia—ALL (RS4-11), Acute myelogenous leukemia—AML (HL-60), Chronic myelogenous leukemia—CML (K562), Chronic lymphocytic leukemia—CLL (MEC-1), Myeloma (KMM1), Burkitt's lymphoma (RAJI), Follicular lymphoma (DOHH2), Breast carcinoma (MDA231), Lung carcinoma (NCI-H520), Prostate carcinoma (PC3), Colon carcinoma (HCT116), Bladder carcinoma (UM-UC-3), Renal cell carcinoma (VMRC-RCW), Skin Melanoma (MEL-1). Tumor cell death was evaluated by Annexin-V staining (n=3, *p<0.05).

DETAILED DESCRIPTION OF THE INVENTION

The disclosed subject matter relates to a cell line of peripheral blood lymphocytes comprising γδ T cells, composition and production method thereof and use in medicine, namely in cancer treatment. These γδ T cells express the Vδ1$^+$ T cell receptor (TCR) and functional natural cytotoxicity receptors (NCRs). NCRs are up regulated in Vδ1$^+$ T cells by AKT-dependent signals provided synergistically by γc-cytokines and Vδ1$^+$ TCR.

The invention discloses a novel Vδ1$^+$ PBL subset capable of targeting hematological tumors highly resistant to fully-activated Vγ9Vδ2 PBLs. This Vδ1$^+$ population owe its specialized killer function to induced expression of natural cytotoxicity receptors, which have been mostly regarded as NK-specific markers. Is shown that, although neither Vδ1$^+$ nor Vδ2$^+$ cells express NCRs constitutively, these can be selectively upregulated in Vδ1$^+$ cells by AKT-dependent signals provided synergistically by γ$_c$-family cytokines and Vδ1$^+$ TCR. It is also shown that NKp30 and NKp44 are both functional in NCR$^+$ Vδ1$^+$ PBLs and critically contribute to their enhanced targeting of lymphocytic leukemia cells.

The disclosed subject matter relates to the combination of γc cytokines and mitogenic (PHA or OKT3) stimuli, to induce NCR expression in a sizeable Vδ1$^+$ PBL subset that is endowed with increased cytolytic activity against hematological tumors. Although PHA is a non-physiological T-cell mitogen, is demonstrated that its effect on NCR induction was fully mimicked by cross-linking the TCR/CD3 complex on Vδ1$^+$ PBL. Thus, NCR induction is coupled to TCR-mediated proliferation of Vδ1$^+$ cells, while also requiring γ$_c$ cytokine signals.

Figure 5:
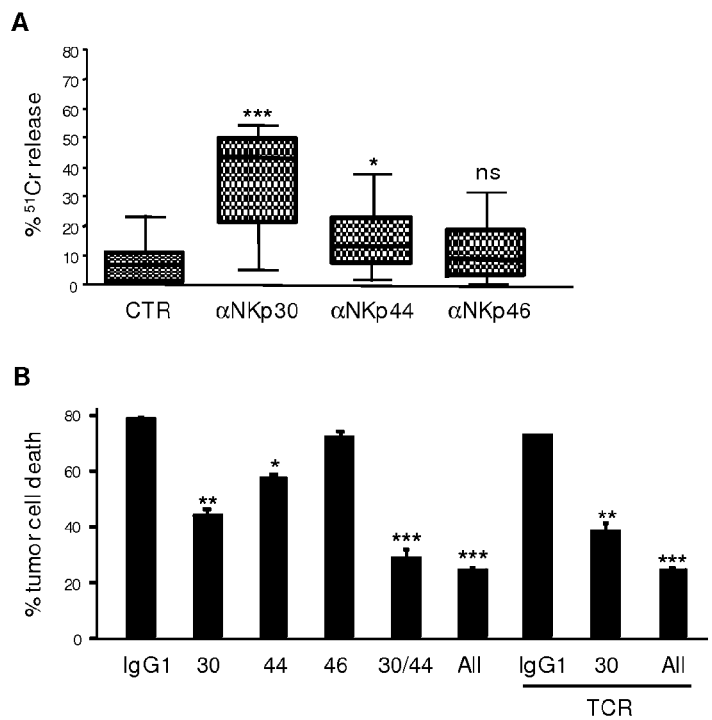
FIG. 5—NKp30 and NKp44 mediate tumor cell killing by NCR$^+$ γδ PBLs. (A) Functional evaluation of NKp30, NKp44 and NKp46 using specific monoclonal antibodies in a 4-hour $^{51}$Cr release redirected killing assay (at 2:1 effector:target ratio) of the FcγR$^+$ P815 target cell line by γδ PBLs activated and expanded with PHA/IL-2. Data are presented as mean and SD of 8 independent experiments performed in triplicate (*p<0.05, ***p<0.001; ns=not statistically significant). (B) Effect of blocking antibodies to NKp30, NKp44 and NKp46 (or control IgG1 isotype control) on killing assays of the leukemia cell line Molt-4 by γδ PBLs activated and expanded with PHA/IL-2. Where noted, blocking anti-TCRγδ mAb (TCR) was also added. Tumor cell death was assessed by Annexin-V staining as described in FIG. 1. Error bars represent SD (n=3, p<0.01; *p<0.001).

Among inducible NCRs, NKp30 is the most important for the anti-tumor activity of Vδ1$^+$ T-cells, based on the proportion of cells that express it (FIG. 3D); the higher enhancement in Vδ1$^+$ T-cell cytotoxicity upon NKp30 triggering (FIG. 5A); and the significant reduction in leukemia cell killing upon NKp30 blockade (FIG. 5B). This notwithstanding, NKp44 (but not NKp46) is also functional in NCR$^+$ Vδ1$^+$ cells (FIG. 5A), and appears to synergize with NKp30 for enhanced tumor targeting (FIG. 5B).

Both NKp30 and NKp44 have been implicated in human NK cell recognition of viral-infected cells. As for tumors, antibody-mediated blocking experiments demonstrated important roles in myeloma and melanoma cell targeting. Moreover, lack of NCR expression has been clinically correlated with poor survival in AML patients.

Vδ1$^+$ T-cells are the predominant γδ T-cell subset during fetal/early life, when they are already able to respond to viral infection. In adults, Vδ1$^+$ T-cell expansions have been associated with CMV infection, HIV-1 infection, and tumors of either epithelial or hematopoietic origin. An attractive prospect for adoptive transfer of activated Vδ1$^+$ T-cells is that they may display particularly good capacity to home to tissues, since, contrary to their circulating Vδ2$^+$ counterparts, Vδ1$^+$ cells are preferentially tissue-associated lymphocytes (Groh, Spies, Science 1998). Interestingly, the abundance of Vδ1$^+$ T-cells at mucosal surfaces has been attributed to IL-15, which induces chromatin modifications that control TCR gene rearrangement.

Figure 3A:
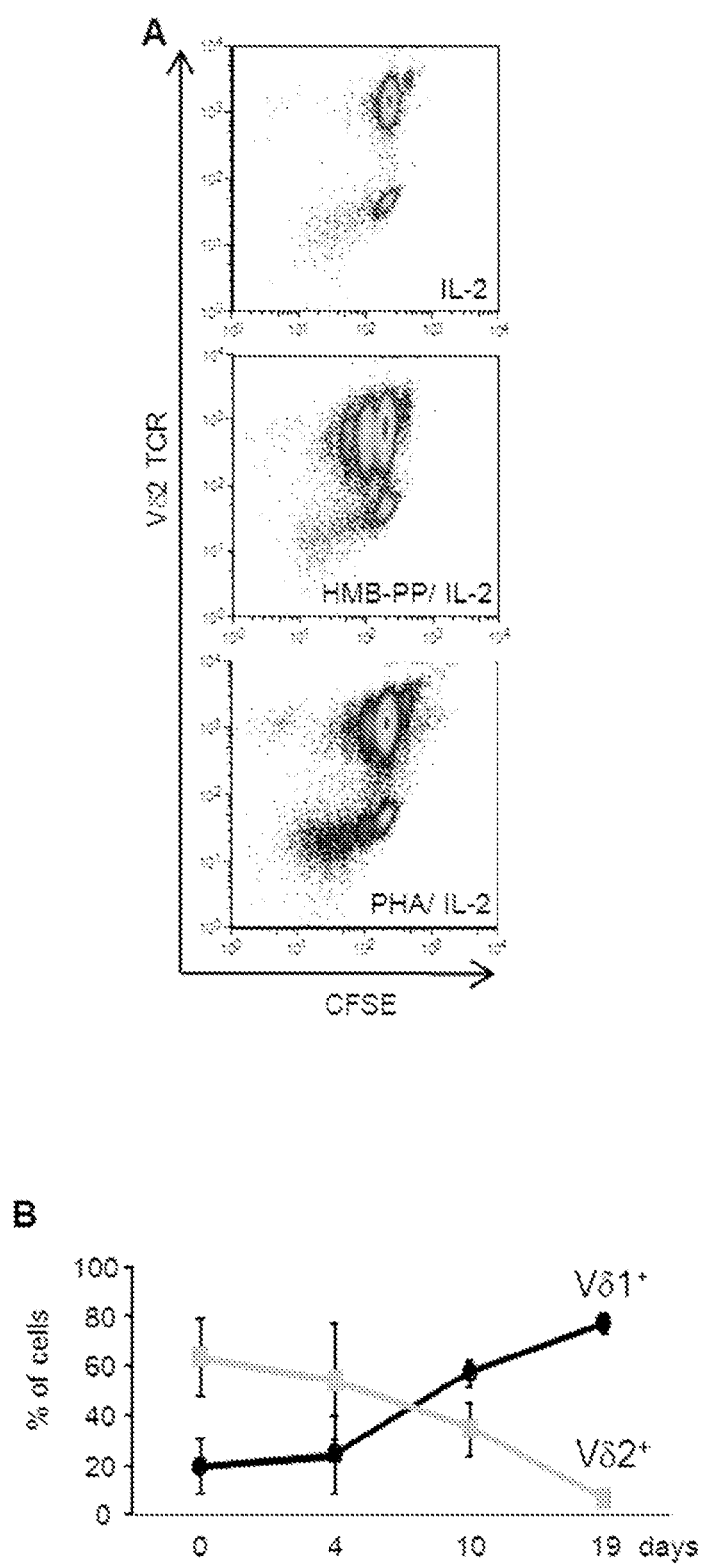
FIGS. 3a, 3b—Natural Cytotoxicity Receptors are selectively expressed on proliferating Vδ1$^+$ T-cells. (A) γδ PBLs were labeled with CFSE and cultured as described in FIG. 1, or in the absence of T cell mitogens (i.e., IL-2 alone). Flow cytometry analysis of CFSE dilution and Vδ2 TCR expression after 7 days in culture. (B) Percentage of Vδ1$^+$ or Vδ2$^+$ cells among total γδ PBLs cultured up to 19 days with PHA/IL-2. Error bars represent SD (n=3). (C) NKp30 expression in PHA/IL-2-activated γδ PBL subsets. Vδ1$^+$ or Vδ2$^+$ cells were FACS-sorted from peripheral blood, labeled with CFSE and cultured with PHA/IL-2 for 7 days. Percentages refer to NKp30$^+$ cells within each cell division (according to CFSE levels and indicated by vertical rectangles). (D) Expression of NKp30, NKp44 and NKp46 in Vδ1$^+$ T-cells after 19 days of PHA/IL-2 stimulation. Isotype mAb control stainings are also shown. Data in this figure are representative of 2-3 independent experiments with similar results.
Figure 3B:
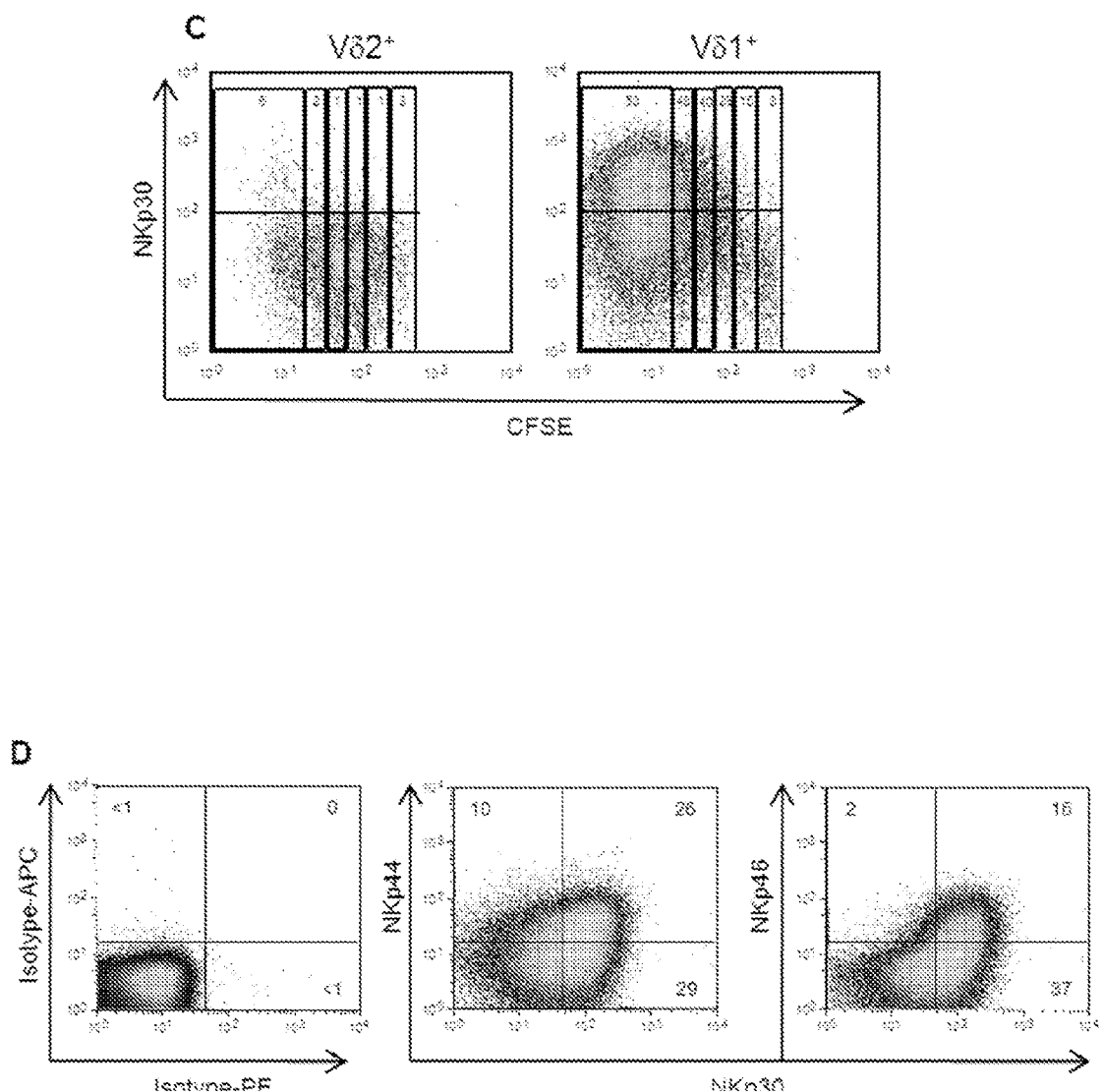

The present invention describes that NCR$^+$ Vδ1$^+$ cells are capable of targeting primary lymphoid leukemic cells, which is particularly interesting taking into account that Vδ1$^+$ T-cells have been previously reported to be inefficient killers of primary leukemia or lymphoma cells. The present invention also discloses the preferential expansion of Vδ1$^+$ T-cells (among γδ PBL) upon PHA treatment in vitro (FIG. 3B). Since this is not due to selective apoptosis of the dominant Vδ2$^+$ counterparts (FIG. 8), it must derive from a proliferative advantage of Vδ1$^+$ cells when receiving PHA-dependent TCR signals (FIGS. 3A-B). It was previously observed that Vδ1$^+$ T-cells express significantly higher levels of the CD27 coreceptor (when compared to Vδ2$^+$ cells). In both humans and mice, CD27 stimulation enhances Cyclin D2 expression and promotes γδ T-cell proliferation in vitro and in vivo.

Figure 4A:
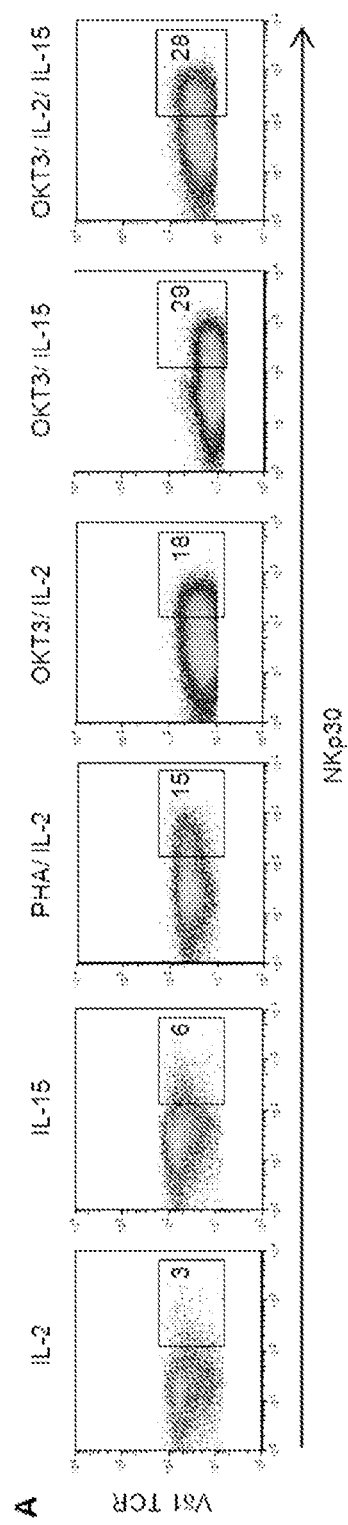
FIGS. 4a, 4b—AKT-dependent γc cytokine and TCR signals induce NKp30 expression in Vδ1$^+$ T-cells. (A-B) Flow cytometry analysis of NKp30 expression on pre-gated Vδ1$^+$ T-cells from γδ PBL cultures after 7 days in the presence of IL-2 or IL-15, alone or in combination with PHA or OKT3 (anti-CD3 mAb). (C) Effect of blocking anti-TCRγδ mAb on NKp30 induction in PHA/IL-2-activated γδ PBLs. Shaded grey are pre-gated NKp30$^+$ cells in 7-day control cultures. (D) Effect of chemical inhibitors LY294002 and UO126 on NKp30 induction in PHA/IL-2-activated γδ PBLs, pre-labeled with CFSE. Data in this figure are representative of 2-3 independent experiments with similar results.
Figure 4B:
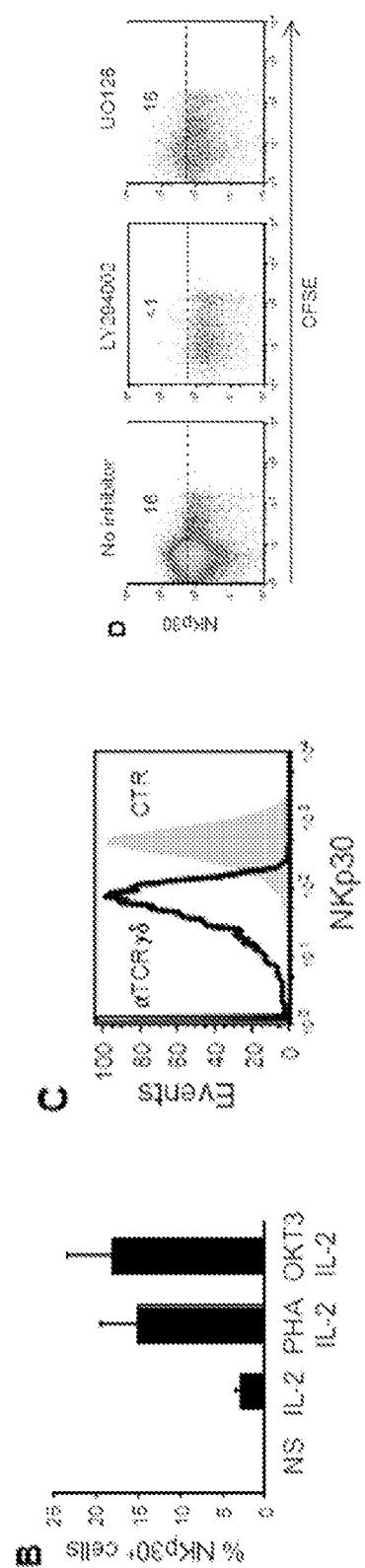

The invention describes that efficient induction of NCR expression on Vδ1$^+$ cells depends on TCR stimulation; in its absence, γ$_c$ cytokines can only effect a very modest upregulation of NCR expression (FIGS. 4A-B). Thus, TCR signals are upstream of NCR-mediated tumor cell recognition by NCR$^+$ Vδ1$^+$ lymphocytes.

In a clinical perspective, this invention describes a method to induce NCR ex vivo, and a very feasible way to expand and inject large numbers of cells into patients. The activation status of these cells could potentially be maintained in vivo, via administration of low doses of IL-2, which appears to be sufficient to sustain NCR expression.

PHA/IL-2 activated NKp30$^+$ γδ T cells preferentially express CD11c and CD8. CD11c is an adhesion molecule usually expressed in other lymphocytes and has been shown to be involved in the recognition of tumor cells.

Materials and Methods

Isolation of Human Peripheral Blood γδ T-Cells.

Peripheral blood was collected from anonymous healthy volunteers, diluted 1:1 (v/v) with PBS (preferably, Invitrogen Gibco) and centrifuged preferably, in Ficol-Paque (preferably, Histopaque-1077, Sigma) in a volume ratio of 1:3 (1 part of ficol for 3 of diluted blood) for 30 minutes at 1500 rpm and 25° C. The interface containing mononuclear cells was collected and washed (in PBS), and γδ T-cells were isolated (to above 95% purity) by magnetic cell sorting via positive selection (preferably, with a FITC-labeled anti-TCRγδ antibody) or via negative selection (with a cocktail of Biotin-labelled antibodies; preferably, Miltenyi Biotec).

Cell Culture.

Isolated γδ PBLs were cultured at 10$^6$ cells/mL at 37° C., 5% $CO_2$ in round-bottom 96 well plates with RPMI 1640 with 2 mM L-Glutamine (preferably, Invitrogen Gibco) supplemented with 10% foetal bovine serum (preferably, Invitrogen Gibco), 1 mM Sodium Pyruvate (Invitrogen Gibco), 50 mg/mL of penicillin/streptomycin (preferably, Invitrogen Gibco). The cells were expanded in the presence of 100 U/ml of rhIL-2 (preferably, Roche Applied Science), with or without 10 nM of HMB-PP (4-hydroxy-3-methyl-but-2-enyl pyrophosphate; preferably, Echelon Biosciences) and 1 μg/ml of Phytohaemagglutinin (PHA; preferably, Sigma-Aldrich). Cells were washed and the culture medium was replaced every 5-6 days. To study the induction of NKp30 expression, γδ PBLs were cultured in the presence or absence of 100 U/ml of rhIL2 (preferably, Roche Applied Science), 1 μg/ml of soluble anti-CD3 antibody (preferably, eBioscience, clone OKT3) and 20 ng/ml of rhIL-15 (preferably, Biolegend). For TCR blockade, freshly-isolated γδPBL were CFSE-labeled and then incubated for 7 days with anti-TCRγδ (preferably, Beckman Coulter, clone IMMU510) diluted 1:20 in complete medium supplemented with 1 μg/ml PHA and 100 U/ml rhIL2. To study the effects of chemical inhibitors of signal transduction, the MEK inhibitor UO126 and the PI-3K inhibitor LY294002 (preferably, both from Calbiochem) were added at 10 mM for a 2-hour incubation period and then maintained in culture with 100 U/ml rhIL2 and 1 μg/ml PHA for 7 days.

Flow Cytometry Cell Sorting.

For sorting of γδ PBL based on the expression of NKp30 and Vδ1$^+$ TCR, cells from PHA/IL-2-activated cultures were stained with anti-NKp30 (preferably, Biolegend, clone P30-15), anti-Vδ1 (preferably, Thermo Fisher Scientific, clone TS8.2) and sorted on a FACSAria cell sorter (preferably, BD Biosciences).

Leukemia Patient Samples.

B-cell chronic lymphocytic leukemia cells were obtained from the peripheral blood of patients at presentation, after informed consent and institutional review board approval (Instituto Português de Oncologia de Lisboa, Portugal). Samples were enriched by density centrifugation over Ficol-Paque and then washed twice in 10% RPMI 1640 (as above).

In Vitro Tumor Killing Assays.

All tumor cell lines were cultured in complete 10% RPMI 1640 (as above), maintained at 10$^5$ up to 10$^6$ cells/mL by dilution and splitting 1:3 every 3-4 days. For cytotoxicity assays, magnetically purified γδ PBL were pre-activated for 7-19 days in the presence of IL-2 (100 U/mL) and either 1 μg/mL PHA or 10 nM HMB-PP. For receptor blocking, γδ PBLs were incubated for 2 h with the blocking antibodies anti-NKp30 (clone F252), anti-NKp44 (clone KS38), anti-NKp46 (clone KL247) or anti-TCR γδ (Beckman Coulter, clone IMMU510). The blocking antibodies were maintained in the culture medium during the killing assays. Tumor cell lines or leukemia primary samples were stained with Cell-Trace Far Red DDAO-SE (1 μM; Molecular Probes, preferably, Invitrogen) and each 3×10$^4$ tumor cells were incubated with 3×10$^5$ γδ T-cells in RPMI, for 3 hrs at 37° C. and 5% $CO_2$ on a round-bottom 96 well plate. Cells were then stained with Annexin V-FITC (preferably, BD Biosciences) and analyzed by flow cytometry. For the redirected killing assays, PHA/IL-2-activated γδ PBL were incubated for 4 hrs with the NCR agonists anti-NKp30 (clone AZ20), anti-Nkp44 (clone 2231) or anti-NKp46 (clone Bab281) during a standard $^{51}$Cr release assay.

Flow Cytometry Analysis.

Cells were labeled with fluorescent monoclonal antibodies: anti-CD3-PerCP-Cy5.5 (preferably, eBioscience, clone OKT3), anti-TCRγδ-FITC (preferably, eBioscience, clone B1.1), anti-CD69-PE (preferably, BD Pharmingen, clone FN50), anti-NKG2D-PE/Cy7 (Biolegend, clone 1D11), anti-2B4-APC (preferably, Biolegend, clone C1.7), anti-DNAM-1-Alexa-Fluor647 (Biolegend, clone DX11), anti-NKp30-APC (preferably, Biolegend, clone P30-15), anti-Vδ2 TCR-PE (preferably, Biolegend, clone B6), anti-NKp44-APC (preferably, Biolegend, clone P44-8), anti-NKp46-AlexaFluor647 (preferably, Biolegend, clone 9E2), anti-Vδ1 TCR-FITC (preferably, Thermo Fisher Scientific, clone TS8.2), anti-NKp30-PE (preferably, Biolegend, clone P30-15), anti-Mouse IgG1κ-APC Isotype Ctrl (preferably, Biolegend, clone MOPC-21), anti-Mouse IgG1κ-PE Isotype Ctrl (preferably, Biolegend, clone MOPC-21), anti-CD27-APC/Cy7 (preferably, Biolegend, clone O323), anti-CD56-APC (preferably, Biolegend, clone HCD56). Cell proliferation was measured by following a standard CFSE staining protocol (preferably, CellTrace CFSE Cell Proliferation Kit, Invitrogen; final concentration 0.5 mM), while apoptosis was assessed by AnnexinV-FITC (preferably, BD Pharmingen) staining. Cells were analyzed on a FACSCanto flow cytometer (preferably, BD Biosciences).

RNA Isolation and cDNA Production.

Total RNA was extracted using the RNeasy Mini Kit according to manufacture's protocol (preferably, Qiagen, Hilden, Germany). Concentration and purity was determined by spectrophotometry and integrity was confirmed using an Agilent 2100 Bioanalyzer with a RNA 6000 Nano Assay (preferably, Agilent Technologies, Palo Alto, Calif.). Total RNA was reverse-transcribed into cDNA using random hexamers and Superscript II first strand synthesis reagents (preferably, Invitrogen).

Real-Time Quantitative PCR (qPCR).

qPCR was performed on ABI Prism 7500 FAST Sequence Detection System using SYBR Green detection system (preferably, both from Applied Biosystems). Primers were designed using Primer3 v.0.4.0 online program (http://primer3.sourceforge.net). For each transcript, quantification was done using the calibration curve method. $β_2$-microglobulin (b2m), Glucoronidase beta (Gusb) and proteasome subunit beta type 6 (Psmb6) were used as housekeeping controls for normalization of gene expression. The following primers were used:

| | |
|---|---|
| b2m - forward | CTAT CCAG CGTA CTCC AAAG ATTC, |
| reverse | CTTG CTGA AAGA CAAG TCTG AATG; |
| Psmb6 - forward | GGCG GCTA CCTT ACTA GCTG, |
| reverse | AAAC TGCA CGGC CATG ATA; |
| Gusb - forward | TGCA GCGG TGTA CTTC TG, |
| reverse | CCTT GACA GAGA TCTG GTAA TCA; |
| B7-H6 - forward | TCAC CAAG AGGC ATTC CGAC CT, |
| reverse | ACCA CCTC ACAT CGGT ACTC TC; |
| Nkp44 - forward | CCGT CAGA TTCT ATCT GGTG GT, |
| reverse | CACA CAGC TCTG GGTC TGG; |
| Nkp46 - forward | AAGA CCCC ACCT TTCC TGA, |
| reverse | TGCT GGCT CGCT CTCT AGT; |
| Gzmb - forward | GGGG GACC CAGA GATT AAAA, |
| reverse | CCAT TGTT TCGT CCAT AGGA G. |

All samples were run in triplicate and repeated three times. Analysis of the qPCR results was performed using the ABI SDS v1.1 sequence analysis software (Applied Biosystems).

Statistical Analysis.

Differences between subpopulations were assessed using Student's t-test and is indicated when significant as $*p<0.05$; $p<0.01$; $*p<0.001$.

Results

Enhanced Cytotoxicity of γδ PBL Cultures Activated with Pan-T-Cell Mitogen

Figure 1B:
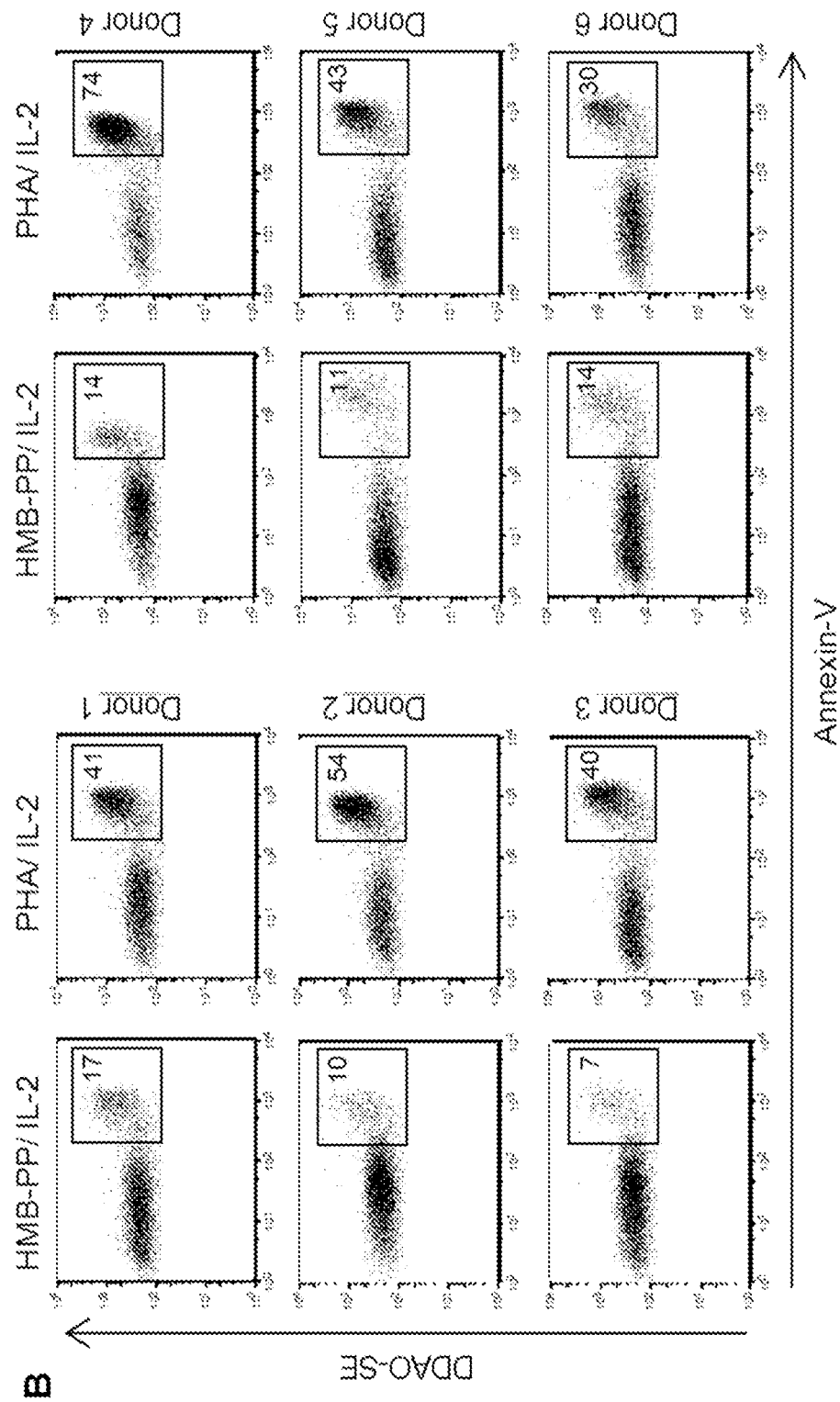
Figure 1C:
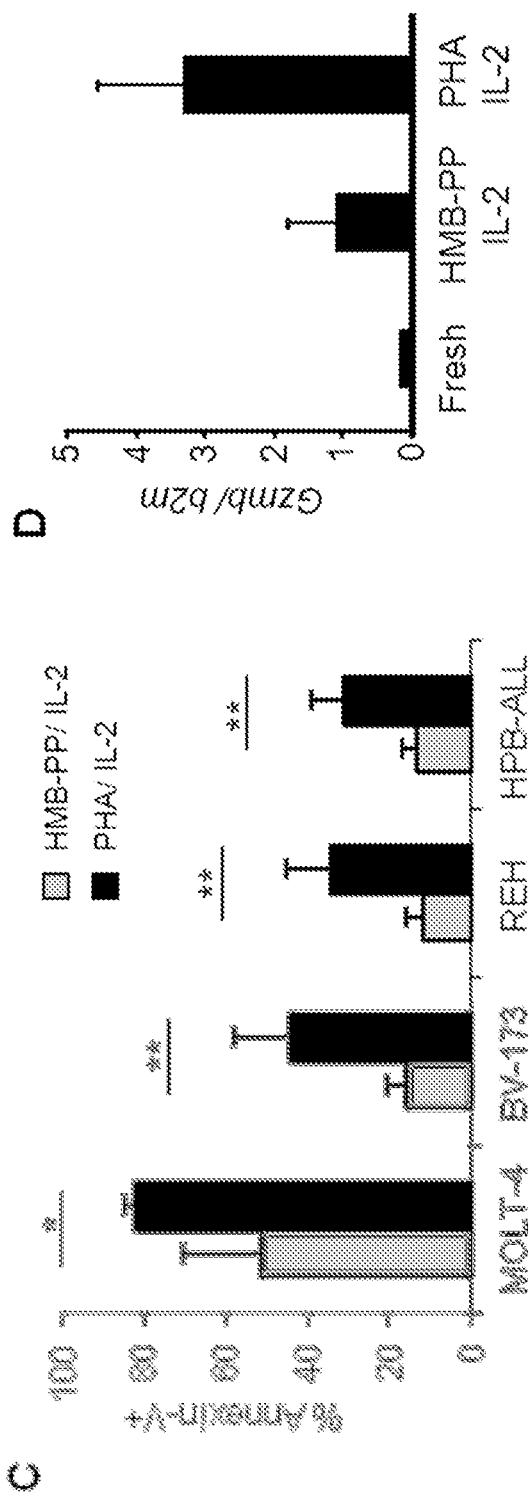

Was compared the anti-tumor killing capacity of γδ PBL cultures (always maintained in the presence of IL-2) activated either with PHA, a plant lectin that acts as a potent T-cell mitogen, or the specific Vγ9Vδ2 TCR agonist HMB-PP (Morita, C. T., Jin, C., Sarikonda, G., and Wang, H. 2007. Nonpeptide antigens, presentation mechanisms, and immunological memory of human Vgamma2Vdelta2 T cells: discriminating friend from foe through the recognition of prenyl pyrophosphate antigens. Immunol Rev 215:59-76). Although both regimens were similarly efficient at activating γδ PBLs, as evaluated by cell proliferation and CD69 upregulation (FIG. 1A), it was noted that samples activated with PHA were consistently better killers of hematopoietic tumor cell lines than samples (of the same donor origin) stimulated with HMB-PP (FIGS. 1B-C). This was valid across all donors tested (FIG. 1B) and was associated with higher expression of Granzyme B (FIG. 1D), a key component of the lymphocyte cytolytic machinery. Of note, freshly-isolated γδ PBLs, which lack Granzyme B expression (FIG. 1D), displayed very poor anti-leukemia cytotoxicity (<10% killing), as previously reported.

The superior cytotoxic function of PHA-stimulated γδ PBL cultures was a surprising finding, since is shown that HMB-PP is a very potent activator of the highly dominant Vγ9Vδ2 PBL subset (Morita, C. T., Jin, C., Sarikonda, G., and Wang, H. 2007. Nonpeptide antigens, presentation mechanisms, and immunological memory of human Vgamma2Vdelta2 T cells: discriminating friend from foe through the recognition of prenyl pyrophosphate antigens. Immunol Rev 215:59-76). Compared to HMB-PP-activated γδ PBL, PHA-stimulated cultures displayed improved cytotoxicity against various resistant leukemia cell lines, such as Bv-173, REH or HPB-ALL (FIGS. 1B-C), which has been shown to lack expression of the critical NKG2D ligand ULBP1. These data demonstrate that the pan-T-cell mitogen PHA is capable of increasing the cytolytic potential of medium-term (1-3 weeks) γδ PBL cultures, which could be of great value for adoptive cell immunotherapy.

Induction of NCR Expression on γδ PBLs Activated with Pan-T-Cell Mitogen

Was investigated the mechanism(s) underlying the enhanced cytotoxicity of PHA-activated γδ PBL cultures.

Figure 2A:
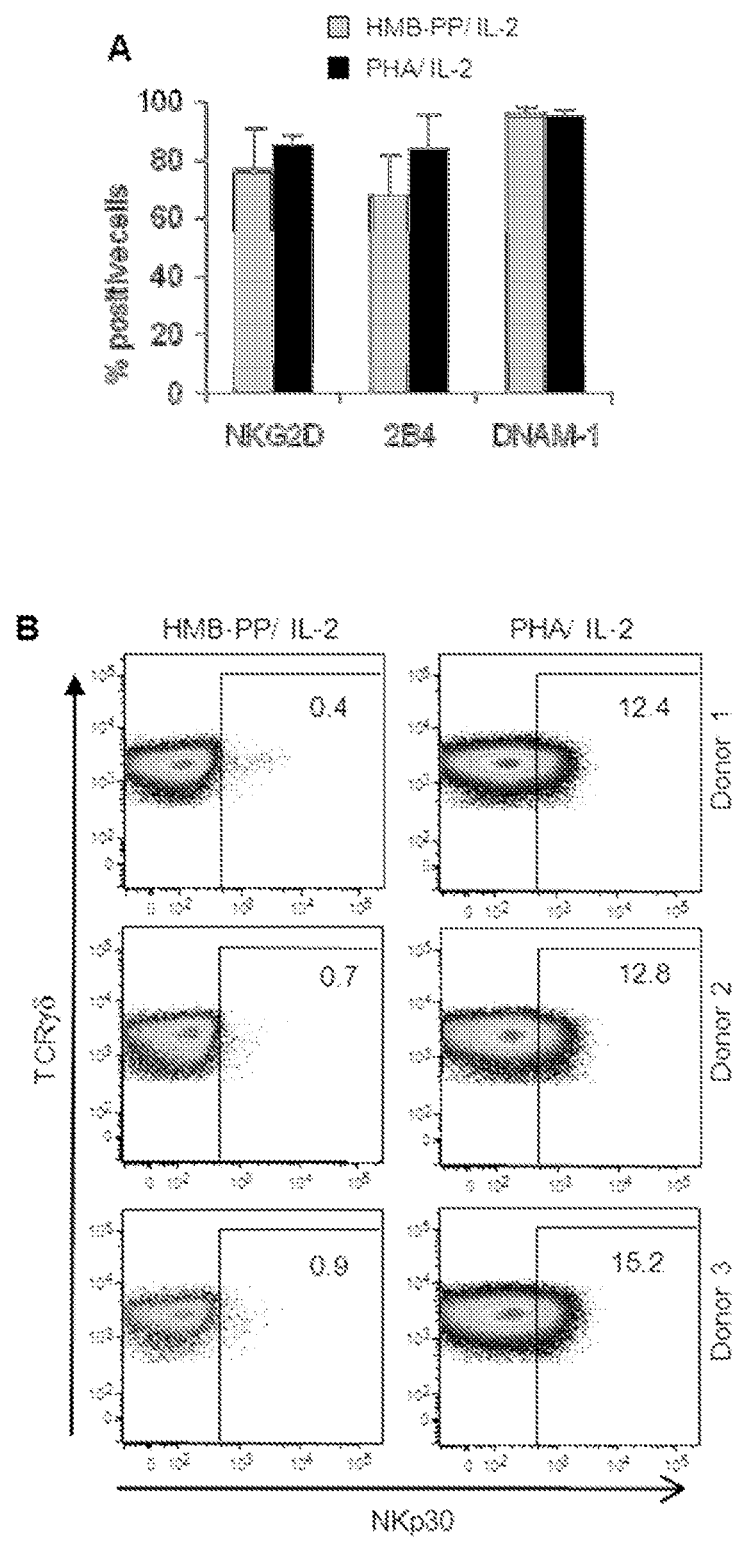
FIGS. 2a, 2b, 2c—Induction of Natural Cytotoxicity Receptor expression in γδ PBLs activated with pan-T-cell mitogen. γδ PBLs were cultured as described in FIG. 1 for 4-19 days, and analyzed by flow cytometry for surface expression of various NK receptors. (A) Results for NKG2D, 2B4 and DNAM-1 in 10-day cultures activated either with HMB-PP/IL-2 (grey) or PHA/IL-2 (black), derived from 6 independent healthy donors. Error bars represent SD (n=6; p>0.05). (B) Expression of NKp30 in the same cultures of (A). FACS plots correspond to cultures derived from 3 individual donors. Percentages refer to NKp30$^+$ γδ PBLs. Isotype control staining is presented in FIG. 7. (C-D) Real-time PCR quantification of Nkp44 (C) and Nkp46 (D) mRNA levels in freshly-isolated, HMB-PP/IL-2-activated and PHA/IL-2-activated γδ PBL. (E) Evolution of the percentage of NKp30$^+$ cells in the cultures described in (A), analyzed up to day 19. Error bars represent SD (n=5). (F) Induction of NKp30 expression in total γδ PBL or in FACS-sorted (>99% pure) NKp30$^{(-)}$ γδ PBL from PHA/IL-2-activated γδ PBL cultures (as in B). Cells were stimulated with PHA/IL-2 for 14 days. Data in this figure are representative of 2-4 independent experiments with similar results.
Figure 2B:
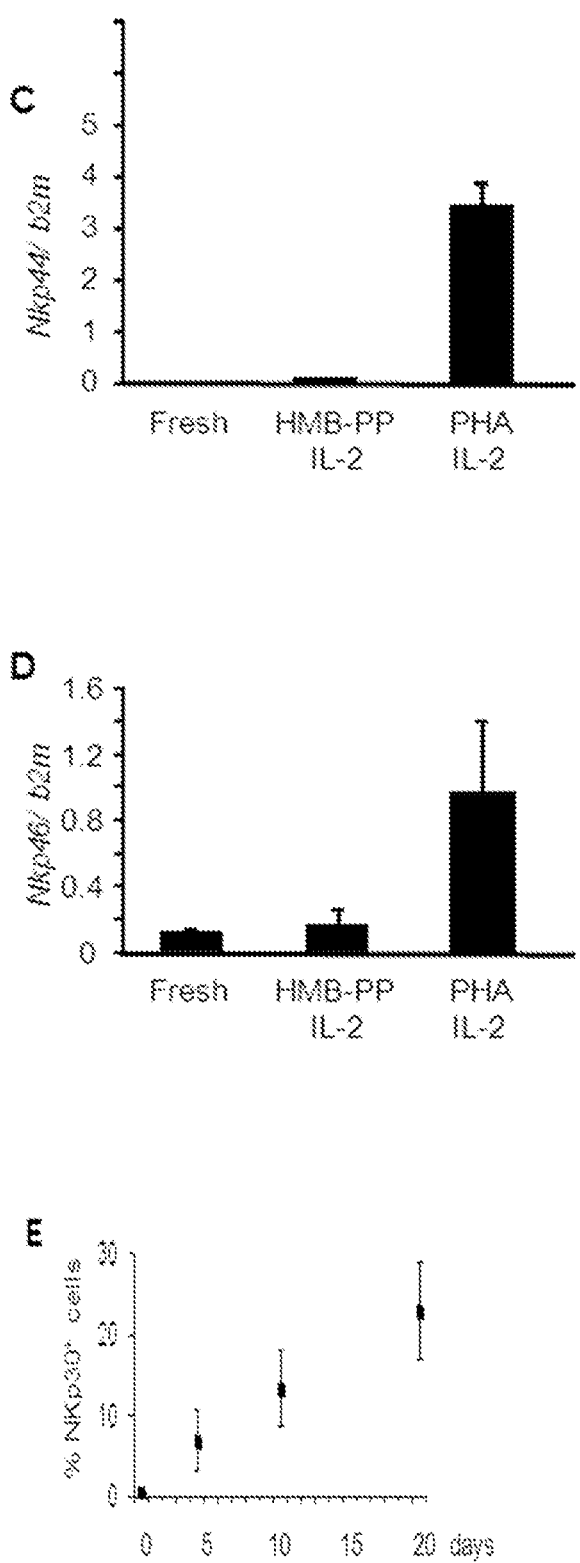
Figure 2C:
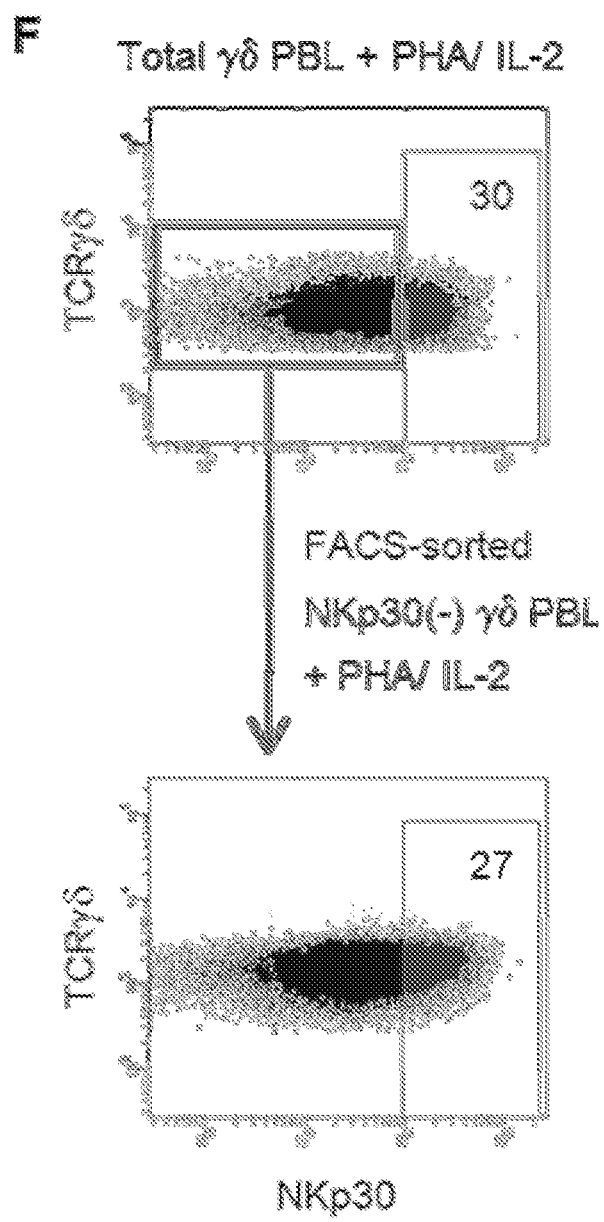

The above data could be explained by the differential expression of receptors such as NKG2D or DNAM-1 or 2B4. All previously were shown to participate in tumor cell recognition by killer lymphocytes. However, none of these candidates was differentially expressed between PHA- and HMB-PP-activated γδ PBL cultures (FIG. 2A). By contrast, and unexpectedly, the natural cytotoxicity receptor NKp30, an important trigger of NK cell cytotoxicity, was specifically found on PHA-stimulated γδ PBLs (FIG. 2B; FIG. 7). Furthermore, the other NCR family members, NKp44 and NKp46, were also selectively expressed in these samples (FIGS. 2C-D; see bellow).

The proportion of NKp30$^+$ cells increased steadily with culture time (FIG. 2E), suggesting an association of NKp30 induction with cell proliferation. Although unlikely due to the very low background in fresh samples (FIG. 2E), it was possible that a minute subset constitutively expressing NKp30 could be preferentially expanded in PHA-stimulated γδ PBL cultures. To address this, were performed experiments with highly (>99%) FACS-purified NKp30$^{(-)}$ cells, which demonstrated that NKp30$^{(-)}$ cells were able to acquire NKp30 expression as efficiently as unsorted cells upon PHA+IL-2 stimulation (FIG. 2F). Moreover, under such conditions, NKp30$^{(-)}$ and NKp30$^+$ cells proliferated to similar extent, further arguing against preferential expansion of NKp30$^+$ cells under such conditions. These results suggest that NKp30 expression is induced de novo upon γδ PBL activation by PHA/IL-2 treatment, which is coupled to cell proliferation.

NCRs are Selectively Expressed by Proliferating Vδ1$^+$ T-Cells

Considering that HMB-PP had been shown to be an optimal agonist of Vγ9Vδ2 cells, although, by contrast with HMB-PP, treatment with PHA preferentially expanded Vδ2$^{(-)}$ cells among γδ PBL (FIG. 3A). This was not due to differences in Vδ2$^+$ cell apoptosis in the two experimental conditions (FIG. 8). The most likely Vδ2$^{(-)}$ population to expand so significantly (FIG. 3A) were Vδ1$^+$ cells, since other subsets are very rare in the peripheral blood of healthy adults. When Vδ1 versus Vδ2 TCR usage was assessed, a dramatic Vδ1$^+$ cell enrichment was found in PHA-activated cultures (>80% of all γδ T-cells after 19 days) (FIG. 3B; FIG. 9). Conversely, and as described, HMB-PP-activated cultures were progressively dominated by Vδ2$^+$ cells (FIG. 3A).

The induction of NKp30 expression was examined in parallel cultures of isolated Vδ1$^+$ or Vδ2$^+$ cells, which were stimulated with PHA+IL-2. While neither freshly isolated Vδ1$^+$ nor Vδ2$^+$ cells expressed NKp30 (FIG. 10), this NCR was strongly induced (upon PHA+IL-2 treatment) in Vδ1$^+$ but not Vδ2$^+$ cells (FIG. 3C). Moreover, by following CFSE dilution was demonstrated a striking accumulation of NKp30$^+$ cells with progressive division of Vδ1$^+$ cells (FIG. 3C). These data suggest that activation of Vδ1$^+$ cells in PHA/IL-2 cultures induces NKp30 expression concomitantly with cell proliferation.

Whereas high percentages (>50%) of NKp30$^+$ cells were usually detected after 2-3 weeks in culture, NKp44 (~30%) and NKp46 (<20%) were expressed in lower proportions of Vδ1$^+$ cells (FIG. 3D). Furthermore, most of NKp44$^+$ or NKp46$^+$ Vδ1$^+$ cells also expressed NKp30 (FIG. 3D). Therefore is considered NKp30 as the most informative marker of the inducible NCR$^+$ Vδ1$^+$ subset.

NCR Induction Requires AKT-Dependent γc Cytokine and TCR Signals

Was dissected the specific signals required for the differentiation of NCR$^+$ Vδ1$^+$ T-cells. First, the two components of the activation protocol, IL-2 and PHA, were dissociated. IL-2, or its related $\gamma_c$ cytokine, IL-15, alone were sufficient to induce some NKp30 expression, but the effect was modest when compared to PHA/IL-2 (or PHA/IL-15) combinations (FIG. 4A). On the other hand, PHA alone was not able to keep the cultures viable, consistent with the critical role of $\gamma_c$ cytokines in the survival of γδ T-cells, particularly upon activation/proliferation.

Although PHA has been a widely used T-cell mitogen, it is also a non-physiological compound capable of cross-linking a series of surface receptors, including the TCR. Thus, the molecular mediator of PHA stimulation could be the Vδ1$^+$ TCR complex. Was compared the ability of PHA and the OKT3 mAb, which specifically cross-links CD3ε chains of the TCR complex, to induce NKp30 expression (when combined with IL-2 or IL-15) in Vδ1$^+$ T-cells. OKT3 was fully capable of mimicking PHA in these assays (FIGS. 4A-B), thus inducing NKp30 in proliferating Vδ1$^+$ T-cells (FIG. 11). Moreover, TCRγδ blockade in PHA/IL-2 cultures prevented NKp30 induction (FIG. 4C). These data suggest that PHA treatment provides TCR signals to induce NCR expression on Vδ1$^+$ PBL. Moreover, the differences between cytokine alone or combination treatments with OKT3 (or PHA) highlight a marked synergy between $\gamma_c$ cytokine and TCR signals in this process (FIGS. 4A-B).

To further explore the molecular mechanisms of NCR induction, was employed chemical inhibitors of key signal transduction pathways downstream of $\gamma_c$ cytokine receptors and/or TCR signaling. While blocking JAK signaling triggered extensive cell death before any NCR induction, co-incubation with the PI-3K/AKT inhibitor LY294002 specifically prevented NKp30 induction in proliferating Vδ1$^+$ T-cells (FIG. 4D). AKT is involved in transducing both $\gamma_c$ cytokine and TCR signals), including TCRγδ signals). By contrast, the MAPK/Erk inhibitor UO126 had no detectable effect on NKp30 induction in proliferating Vδ1$^+$ T-cells (FIG. 4D). Importantly, the selective effect of LY294002 dissociated NCR induction from cell proliferation, thus demonstrating that Vδ1$^+$ T-cell proliferation is necessary (FIG. 3C; FIG. 11) but not sufficient (FIG. 4D) to induce NKp30 expression. Collectively, these data demonstrate that AKT-dependent $\gamma_c$ cytokine and TCR signals synergize to induce NKp30 expression in Vδ1$^+$ T-cells.

Functional NKp30 and NKp44 Trigger Tumor Cell Killing by Vδ1$^+$ PBLs

Were undertooked gain- and loss-of-function experiments to evaluate the impact of NCR modulation on Vδ1$^+$ enriched (>80%; FIG. 9A) PBL cultures, which expressed NCRs at levels similar to those in FIG. 3D. First, by using a reverse Ab-dependent cytotoxicity assay, was showed that cross-linking of NKp30 or NKp44, but not NKp46, produced highly significant increases in lysis of the P815 tumor cell targets (FIG. 5A). These data demonstrate that induced NKp30 and NKp44 are functional and mediate tumor cell killing. To assess if they played non-redundant roles in targeting leukemia cells, was performed receptor blockade experiments using NCR-specific mAbs. Was observed significant reductions in tumor cell lysis upon NKp30 and NKp44 blockade (FIG. 5B). As expected from the results in FIG. 5A, NKp46 blockade did not affect tumor cell killing. Interestingly, a synergistic effect between NKp30 and NKp44 was also clearly observed. Of note, TCRγδ blockade in any setting (alone or in combination with anti-NCR mAbs) was a neutral event during the killing assay (FIG. 5B). These data suggest that leukemia cell targeting by NCR$^+$ Vδ1$^+$ PBLs is a TCR-independent event mostly mediated by the synergistic function of NKp30 and NKp44.

NCR+ Vδ1+ PBL are Specialized Killers that Target Resistant Primary Lymphocytic Leukemias To fully characterize the anti-tumor potential of NCR+ Vδ1+ PBL, NKp30+ cells were FACS-sorted to high degree of purity (>99%) (FIG. 6A) and a series of functional assays were performed. As expected (FIG. 3D), sorted NKp30+ cells also expressed NKp44 and NKp46 (FIG. 6B), and the three NCRs were largely stable on the surface of the purified cells when cultured for two weeks with IL-2 alone (FIG. 6C). These data demonstrate the feasible expansion of a stable NCR+ Vδ1+ T-cell subset.

When the cytotoxic function of NKp30+ cells was assessed, an increased targeting of the resistant leukemia cell line Bv173 (among others) was observed (in comparison with NKp30(−) counterparts) (FIG. 6D). This correlated with higher expression of Granzyme B (FIG. 6E). Moreover, NKp30 expression also associated with higher degree of CD56 expression (FIG. 12), which has been previously linked to cytotoxicity of human lymphocytes, including Vδ2+ T-cells.

Finally, were performed functional killing assays with primary samples obtained from chronic lymphocytic leukemia patients. Importantly, HMB-PP/IL-2-activated γδ PBLs do not express NCRs (FIG. 2B). Was compared their anti-tumor cytolytic activity with that of NCR+ cells isolated from γδ PBL cultures activated with PHA/IL-2. Was observed that NCR+ γδ PBLs, obtained from 6 different donors, were consistently more efficient at eliminating primary B-CLL cells (FIGS. 6F-G).

The invention is of course not in any way restricted to the embodiments described and a person with ordinary skill in the art will foresee many possibilities to modifications thereof without departing from the basic idea of the invention as defined in the appended claims.

The following claims set out particular embodiments of the invention.

The invention claimed is:

1. A cell line of lymphocytes comprising Vδ1+ γδ T cells expressing functional natural cytotoxicity receptors, wherein the natural cytotoxicity receptors comprise NKp30.

2. The cell line according to claim 1 consisting of Vδ1+ γδ T cells expressing functional natural cytotoxicity receptors.

3. The cell line according to claim 1 further comprising Vδ2+ γδ T cells.

4. The cell line according to claim 1 wherein the said lymphocytes are from a peripheral blood sample.

5. The cell line according to claim 1 wherein the natural cytotoxicity receptors comprise NKp44.

6. The cell line according to claim 1 wherein the natural cytotoxicity receptors comprise NKp46.

7. The cell line according to claim 1 comprising cells expressing granzime B.

8. A composition comprising cells of the cell line according to claim 1.

9. A method for treating a subject, including injecting the composition according to claim 8 into the subject.

10. A method for treating a subject, including administering medicine comprising the composition according to claim 8 to the subject.

11. A method for treating a subject, including administering the composition according to claim 8 to the subject in at least one of autologous or heterologous adoptive cell therapy, tumor or cancer treatment, tumor or cancer immunotherapy, and/or leukemia treatment.

12. A method for treating a subject, including administering the composition according to claim 8 to the subject in treatment of acute lymphoblastic leukemia, acute myelogenous leukemia, chronic myelogenous leukemia, chronic lymphocytic leukemia, multiple myeloma, burkitt's lymphoma, follicular lymphoma, breast carcinoma, lung carcinoma, prostate carcinoma, colon carcinoma, bladder carcinoma, renal cell carcinoma, or skin melanoma.

13. A method for treating a subject, including administering the composition according to claim 8 to the subject in treatment of a viral infection.

14. The method according to claim 13 wherein the virus is from the family Herpesviridae or Retroviridae.

15. A method of producing a cell line described in claim 1 which comprises isolating γδ PBLs and cultivating these cells in adequate culture medium, with regular addition of γδTCR agonists and IL-2, IL-15, or mixtures thereof is carried out until at least 40% of the cells express natural cytotoxicity receptors.

16. The method according to claim 15 wherein the regular addition of said γδTCR agonists and cytokines is carried out until at least 40% of the cells express NKp30.

17. The method according to claim 15 wherein the γδTCR agonist is phytohemagglutinin-PHA, anti-CD3 monoclonal antibody, anti-γδTCR monoclonal antibody or mixtures thereof.

18. The method according to claim 17 wherein the range of γδTCR agonist concentration is 0.01-100 μg/ml.

19. The method according to claim 15, wherein the range of IL-2 and IL-15 concentrations is 1-10000 U/ml.

20. The method according to claim 19 wherein the range of IL-2 and IL-15 concentrations is 100-1000 U/ml.

21. The method according to claim 15 wherein the time range of the addition of said γδTCR agonists and cytokines is 2-60 days.

22. The method according to claim 21 wherein the time range of the addition of said γδTCR agonists and cytokines is 9-25 days.

23. The method according to claim 22 wherein the time range of the addition of said γδTCR agonists and cytokines is 10-15 days.

* * * * *

SEQUENCE LISTING

```
<160> NUMBER OF SEQ ID NOS: 14

<210> SEQ ID NO 1
<211> LENGTH: 24
<212> TYPE: DNA
<213> ORGANISM: Homo sapiens

<400> SEQUENCE: 1
ctatccagcg tactccaaag attc                                          24

<210> SEQ ID NO 2
<211> LENGTH: 24
<212> TYPE: DNA
<213> ORGANISM: Homo sapiens

<400> SEQUENCE: 2
cttgctgaaa gacaagtctg aatg                                          24

<210> SEQ ID NO 3
<211> LENGTH: 20
<212> TYPE: DNA
<213> ORGANISM: Homo sapiens

<400> SEQUENCE: 3
ggcggctacc ttactagctg                                               20

<210> SEQ ID NO 4
<211> LENGTH: 19
<212> TYPE: DNA
<213> ORGANISM: Homo sapiens

<400> SEQUENCE: 4
aaactgcacg gccatgata                                                19

<210> SEQ ID NO 5
<211> LENGTH: 18
<212> TYPE: DNA
<213> ORGANISM: Homo sapiens

<400> SEQUENCE: 5
tgcagcggtg tacttctg                                                 18

<210> SEQ ID NO 6
<211> LENGTH: 23
```

-continued

```
<212> TYPE: DNA
<213> ORGANISM: Homo sapiens

<400> SEQUENCE: 6
ccttgacaga gatctggtaa tca                                           23

<210> SEQ ID NO 7
<211> LENGTH: 22
<212> TYPE: DNA
<213> ORGANISM: Homo sapiens

<400> SEQUENCE: 7
tcaccaagag gcattccgac ct                                            22

<210> SEQ ID NO 8
<211> LENGTH: 22
<212> TYPE: DNA
<213> ORGANISM: Homo sapiens

<400> SEQUENCE: 8
accacctcac atcggtactc tc                                            22

<210> SEQ ID NO 9
<211> LENGTH: 22
<212> TYPE: DNA
<213> ORGANISM: Homo sapiens

<400> SEQUENCE: 9
ccgtcagatt ctatctggtg gt                                            22

<210> SEQ ID NO 10
<211> LENGTH: 19
<212> TYPE: DNA
<213> ORGANISM: Homo sapiens

<400> SEQUENCE: 10
cacacagctc tgggtctgg                                                19

<210> SEQ ID NO 11
<211> LENGTH: 19
<212> TYPE: DNA
<213> ORGANISM: Homo sapiens

<400> SEQUENCE: 11
aagaccccac ctttcctga                                                19

<210> SEQ ID NO 12
<211> LENGTH: 19
<212> TYPE: DNA
<213> ORGANISM: Homo sapiens

<400> SEQUENCE: 12
tgctggctcg ctctctagt                                                19

<210> SEQ ID NO 13
<211> LENGTH: 20
<212> TYPE: DNA
<213> ORGANISM: Homo sapiens

<400> SEQUENCE: 13
gggggaccca gagattaaaa                                               20

<210> SEQ ID NO 14
```

```
<211> LENGTH: 21
<212> TYPE: DNA
<213> ORGANISM: Homo sapiens

<400> SEQUENCE: 14
ccattgtttc gtccatagga g                                              21
```